(12) United States Patent
Umezawa et al.

(10) Patent No.: US 11,529,057 B2
(45) Date of Patent: Dec. 20, 2022

(54) PHOTOACOUSTIC APPARATUS, INFORMATION PROCESSING METHOD, AND PROGRAM

(71) Applicant: CANON KABUSHIKI KAISHA, Tokyo (JP)

(72) Inventors: Kohtaro Umezawa, Tokyo (JP); Ryuichi Nanaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1202 days.

(21) Appl. No.: 15/716,150

(22) Filed: Sep. 26, 2017

(65) Prior Publication Data
US 2018/0085005 A1    Mar. 29, 2018

(30) Foreign Application Priority Data

Sep. 27, 2016 (JP) .............................. JP2016-188408

(51) Int. Cl.
*A61B 5/00*      (2006.01)
*A61B 5/145*    (2006.01)
(Continued)

(52) U.S. Cl.
CPC ........ *A61B 5/0095* (2013.01); *A61B 5/14542* (2013.01); *A61B 5/7278* (2013.01);
(Continued)

(58) Field of Classification Search
CPC . A61B 5/0095; A61B 5/14542; A61B 5/7278; A61B 5/742; A61B 5/7475; A61B 2576/00; G06T 5/006; G06T 5/50
See application file for complete search history.

(56) References Cited

U.S. PATENT DOCUMENTS

| 8,977,337 B2 | 3/2015 | Oyama |
| 9,339,254 B2 | 5/2016 | Wanda |

(Continued)

FOREIGN PATENT DOCUMENTS

| EP | 2749209 A1 | 7/2014 |
| EP | 2954839 A1 | 12/2015 |

(Continued)

OTHER PUBLICATIONS

Minghua Xu, et al.; Universal back-projection algorithm for photoacoustic computed tomography; Physical Review E; Jan. 19, 2005; pp. 016706-1-016706-7; American Physical Society; College Park, Maryland, USA.

(Continued)

*Primary Examiner* — Patricia J Park
(74) *Attorney, Agent, or Firm* — Canon U.S.A., Inc. IP Division

(57) ABSTRACT

A photoacoustic apparatus according to the present invention is a photoacoustic apparatus for obtaining image data based on an acoustic wave generated by irradiating an object with light of a first wavelength and light of a second wavelength which is different from the first wavelength, the photoacoustic apparatus including a processing unit configured to: obtain a first image data group corresponding to the first wavelength generated based on an acoustic wave generated by irradiating the object with light of the first wavelength a plurality of times, obtain first positional deviation information corresponding to an irradiation timing with the light of the first wavelength on the basis of a first image data group corresponding to the first wavelength, and obtain second positional deviation information corresponding to an irradiation timing with the light of the second wavelength on the basis of the first positional deviation information.

11 Claims, 15 Drawing Sheets

(51) Int. Cl.
G06T 5/00 (2006.01)
G06T 5/50 (2006.01)
(52) U.S. Cl.
CPC ............ *A61B 5/742* (2013.01); *A61B 5/7475* (2013.01); *G06T 5/006* (2013.01); *G06T 5/50* (2013.01); *A61B 2576/00* (2013.01)

(56) References Cited

U.S. PATENT DOCUMENTS

| | | |
|---|---|---|
| 2012/0289812 A1 | 11/2012 | Oishi |
| 2013/0188707 A1 | 7/2013 | Shimizu et al. |
| 2013/0281819 A1* | 10/2013 | Schmid ................ A61B 8/4281 600/407 |
| 2014/0018645 A1 | 1/2014 | Wada et al. |
| 2014/0202247 A1 | 7/2014 | Kasamatsu et al. |
| 2014/0316236 A1* | 10/2014 | Umezawa ............... A61B 5/742 600/407 |
| 2015/0057534 A1 | 2/2015 | Tsujita |
| 2015/0359434 A1 | 12/2015 | Umezawa |
| 2016/0123810 A1* | 5/2016 | Ando ....................... G01J 3/14 356/326 |
| 2018/0084997 A1 | 3/2018 | Umezawa et al. |
| 2018/0085005 A1 | 3/2018 | Umezawa et al. |
| 2018/0088086 A1 | 3/2018 | Umezawa et al. |

FOREIGN PATENT DOCUMENTS

| | | |
|---|---|---|
| JP | 2014140716 A | 8/2014 |
| JP | 2016019847 A | 2/2016 |
| KR | 10-2015-0121872 A | 10/2015 |
| WO | 2012137855 A1 | 10/2012 |
| WO | 2013188707 A1 | 12/2013 |
| WO | 2014115214 A1 | 7/2014 |

OTHER PUBLICATIONS

Y. Ueda, et al.; Development of optical mammography based on analysis of time-resolved photon path distribution; Proc of SPIE.; 2010; vol. 7561; pp. 756117-1-756117-6; SPIE.; USA.

* cited by examiner

PHOTOACOUSTIC APPARATUS, INFORMATION PROCESSING METHOD, AND PROGRAM

BACKGROUND OF THE INVENTION

Field of the Invention

The present invention relates to a photoacoustic apparatus.

Description of the Related Art

In the field of medicine, research on imaging of functional information, which is physiological information of a living body, has been conducted in recent years. There is photoacoustic imaging (PAI) as one of imaging techniques of functional information.

In the photoacoustic imaging, the object is irradiated with light. The irradiation light propagates and diffuses through the object, and energy of the irradiation light is absorbed in the object. As a result, an acoustic wave (hereinafter referred to as photoacoustic waves) is generated by a photoacoustic effect. By analyzing a received signal of this photoacoustic wave, a spatial distribution of optical characteristic values inside the object is obtained as image data.

In a case where image data is generated based on photoacoustic waves generated by irradiating an object a plurality of times with light, when a relative position between the object and a probe varies during a plurality of light irradiations, the resolution of the image data is lowered.

Japanese Patent Application Laid-Open No. 2014-140716 discusses a technique for estimating the variation amount of a relative position between an object and a probe by calculating the amount of positional deviation between a plurality of image data obtained by a plurality of light irradiations. Furthermore, Japanese Patent Application Laid-open No. 2014-140716 discusses a technique for aligning a plurality of image data based on the variation amount of the estimated relative position.

In the photoacoustic imaging, functional information can be obtained by irradiating an object with light of a plurality of different wavelengths.

However, when generating a plurality of image data based on photoacoustic waves generated by irradiation with light of each of a plurality of wavelengths, there may be a case where a positional deviation occurs among a plurality of image data.

SUMMARY OF THE INVENTION

The present invention is directed to providing an apparatus capable of accurately estimating positional deviation information between a plurality of image data when generating an image data group (a plurality of image data) based on photoacoustic waves generated by irradiation with light of a plurality of wavelengths. That is, the present invention is directed to an apparatus capable of accurately estimating a variation amount of a relative position between an object and a probe even when an image data group is generated on the basis of a photoacoustic wave generated by irradiation with light of a plurality of wavelengths.

A photoacoustic apparatus according to the present invention is a photoacoustic apparatus obtaining image data based on an acoustic wave generated by irradiating an object with light of a first wavelength and light of a second wavelength which is different from the first wavelength, the photoacoustic apparatus including a processing unit configured to obtain a first image data group corresponding to the first wavelength generated based on an acoustic wave generated by irradiating the object with light of the first wavelength a plurality of times, obtain first positional deviation information corresponding to an irradiation timing of the light of the first wavelength on the basis of a first image data group corresponding to the first wavelength, and obtain second positional deviation information corresponding to an irradiation timing with the light of the second wavelength on the basis of the first positional deviation information.

Further features of the present invention will become apparent from the following description of exemplary embodiments with reference to the attached drawings.

DESCRIPTION OF THE EMBODIMENTS

Figure 1:
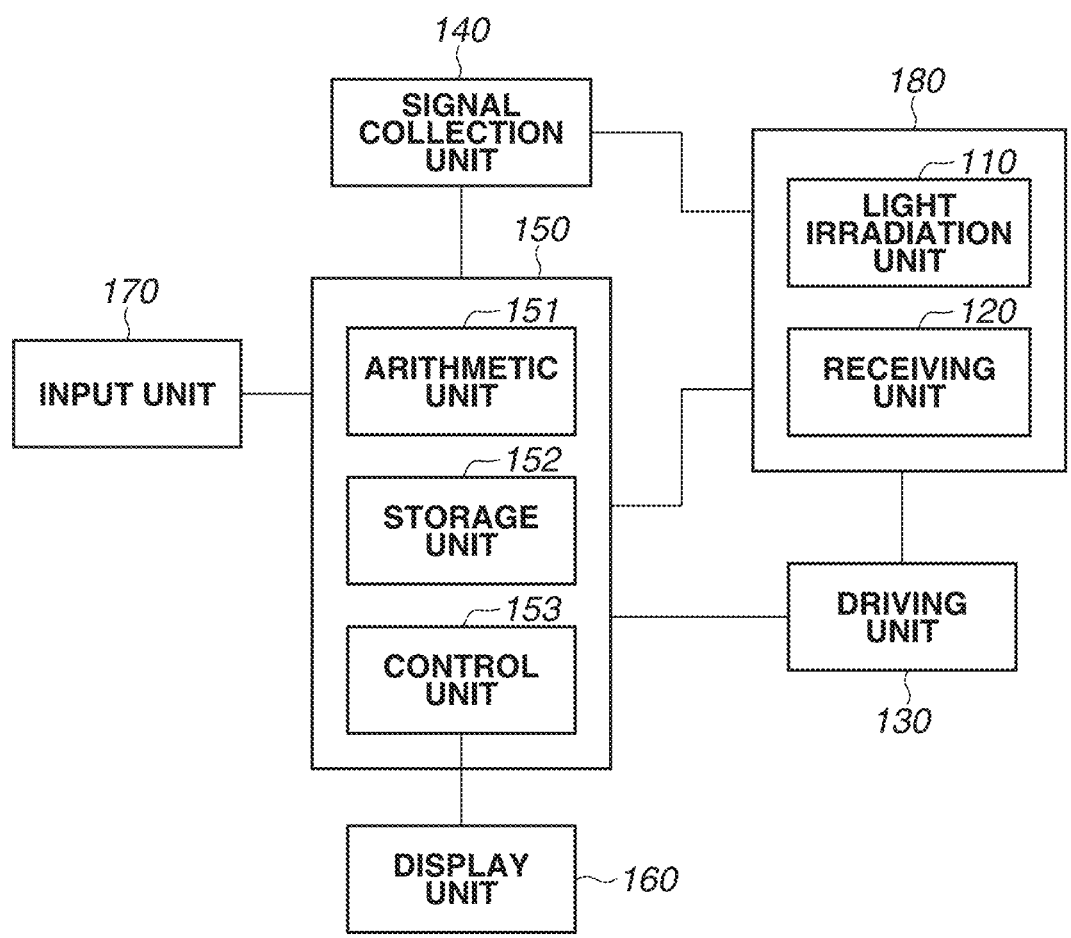
FIG. 1 is a schematic diagram illustrating the configuration of a photoacoustic apparatus according to a first exemplary embodiment.

Hereinafter, an exemplary embodiment of the present invention will be described with reference to the drawings. The same reference numerals are attached to the same constituent elements in principle, and a description thereof is omitted. Each of the embodiments of the present invention described below can be implemented solely or as a combination of a plurality of the embodiments or features thereof where necessary or where the combination of elements or features from individual embodiments in a single embodiment is beneficial.

The first exemplary embodiment will be described below. In this specification, a phenomenon in which a relative position between an imaging target and a probe varies is referred to as "positional deviation". Furthermore, a variation amount of the relative position between the imaging target and the probe is referred to as "positional deviation amount". Furthermore, the amount of change in the position of the imaging target occurring in the image data group (a plurality of image data) due to the positional deviation is referred to as "a positional deviation amount between the plurality of image data". A parameter representing a positional deviation such as translation amount, rotation amount, and deformation amount is referred to as "positional deviation information".

A positional deviation is caused by movement of the object and movement of the probe during a plurality of light irradiations. For example, the probe moves as a user grips and scans a handheld probe or the scanning unit mechanically scans the probe. Due to these positional deviations, when image data is generated based on photoacoustic waves generated by a plurality of light irradiations, a resolution is lowered.

The intensity of the photoacoustic wave generated by light irradiation is determined in proportion to the absorption coefficient of the imaging target. Furthermore, the absorption coefficient has wavelength dependency; therefore, even if the light fluence is the same for each wavelength, the intensity of the generated photoacoustic wave changes depending on the wavelength.

On the other hand, as discussed in Japanese Patent Application Laid-Open No. 2014-140716, when estimating a positional deviation between a plurality of image data, if the image intensities of the same imaging target differ between the plurality of image data, the estimation accuracy of the positional deviation may decrease. Therefore, when the positional deviation amount is to be estimated by using the image data group obtained by irradiation with light of each of mutually different wavelengths, the estimation accuracy of the positional deviation sometimes deteriorates due to differences in image intensity and resolution between wavelengths, and the like.

Therefore, in the photoacoustic apparatus according to one exemplary embodiment of the present invention, positional deviation information between a plurality of image data corresponding to a part of mutually different wavelengths is obtained, and the positional deviation information is used to obtain positional deviation information corresponding to other wavelengths. Thus, since positional deviation information corresponding to a plurality of wavelengths is estimated based on positional deviation information corresponding to a specific wavelength, it is possible to suppress the influence on the obtaining accuracy of the positional deviation information due to the difference in the image intensity between the wavelengths. In addition, by obtaining positional deviation information corresponding to a specific wavelength and obtaining positional deviation information corresponding to other wavelengths by interpolation, it is possible to reduce the amount of processing required to obtain positional deviation information corresponding to the other wavelengths.

That is, in the photoacoustic apparatus according to one exemplary embodiment of the present invention, the object is irradiated with light of the first wavelength and light of the second wavelength which are different from each other, a plurality of times. Then, a first image data group corresponding to the first wavelength is generated, and positional deviation information between the plurality of first image data is obtained. The obtained positional deviation information corresponds to a variation amount (positional deviation amount) of the relative position between the object and the probe corresponding to the irradiation timing with the light of the first wavelength. Then, based on the first positional deviation information, the variation amount (positional deviation amount) between the object and the probe corresponding to the irradiation timing with the light of the second wavelength is estimated.

Furthermore, in the photoacoustic apparatus according to one exemplary embodiment of the present invention, functional information is obtained based on the positional deviation information corresponding to the irradiation with light of a plurality of wavelengths estimated as described above, and received data (signal group or image data) caused by a photoacoustic wave generated by the light irradiation of a plurality of wavelengths. Examples of the functional information include information indicating concentrations of substances such as oxyhemoglobin concentration, deoxyhemoglobin concentration, total hemoglobin amount, oxygen saturation level, and the like. The total hemoglobin amount is a total amount of the sum of oxyhemoglobin and deoxyhemoglobin. Oxygen saturation is the ratio of oxyhemoglobin to total hemoglobin.

The functional information is not limited to image data representing a spatial distribution, but may be information representing a numerical value or a character. For example, the functional information is a concept including information such as the average concentration of substances constituting an object, the value of a specific position in a spatial distribution of a substance concentration at a specific position, and a statistical value (average value, median value, and the like) of pixel values of a spatial distribution of a substance concentration. For example, as an image illustrating the functional information, the numerical value of the average concentration of the substance constituting the object may be displayed on a display unit 160.

In one exemplary embodiment of the invention, based on the image data group obtained by utilizing light of the wavelength in which a molar absorption coefficient of oxyhemoglobin and a molar absorption coefficient of deoxyhemoglobin are the same, positional deviation information may be obtained. When a blood vessel is a measurement object, since the intensity of the photoacoustic wave generated from the blood vessel using light of such a wavelength does not depend on an oxygen saturation degree, a variation in the image intensity for each blood vessel becomes small. Therefore, if light of such a wavelength is used, there is a tendency that the estimation accuracy of the positional deviation information increases. It is to be noted that the molar absorption coefficient of oxyhemoglobin and the molar absorption coefficient of deoxyhemoglobin are not limited to perfectly equal wavelengths (wavelengths having isosbestic point). Even if coefficients are those of substantially equal wavelengths, the estimation accuracy of the positional deviation information tends to be high. For example, a wavelength within ±10 nm of the wavelength of the isosbestic point may be adopted as a substantially equal wavelength. Furthermore, for example, when wavelengths of the molar absorption coefficient of oxyhemoglobin and the molar absorption coefficient of deoxyhemoglobin are within ±10% of the isosbestic point, such wavelengths may be adopted as substantially equal wavelengths. That is, it is preferable to obtain positional deviation information corresponding to other wavelengths based on the positional deviation information obtained by utilizing the light with the wavelength suitable for obtaining the positional deviation information.

Hereinafter, the configuration and processing of the photoacoustic apparatus according to the first exemplary embodiment will be described.

In the present exemplary embodiment, an example using the photoacoustic apparatus will be described. The configuration of the photoacoustic apparatus according to the present exemplary embodiment will be described with reference to FIG. 1. FIG. 1 is a schematic block diagram of the entire photoacoustic apparatus. The photoacoustic apparatus according to the present exemplary embodiment includes a driving unit 130, a signal collection unit 140, a computer 150, the display unit 160, an input unit 170, and a probe 180.

Figure 2:
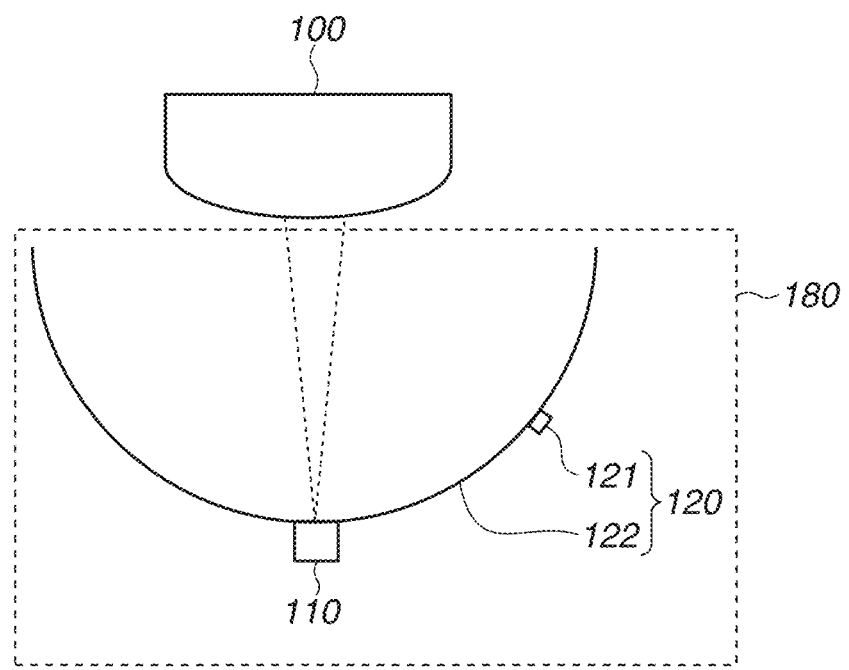
FIG. 2 is a schematic diagram of probe according to the first exemplary embodiment.

FIG. 2 is a schematic diagram of the probe 180 according to the present exemplary embodiment. The probe 180 includes a light irradiation unit 110 and a receiving unit 120. The measurement target is an object 100.

The driving unit 130 drives the light irradiation unit 110 and the receiving unit 120 to perform mechanical scanning. The light irradiation unit 110 irradiates the object 100 with pulsed light, and an acoustic wave is generated within the object 100. An acoustic wave generated by a photoacoustic effect due to light is also referred to as a photoacoustic wave. The receiving unit 120 outputs an electric signal (photoacoustic signal) as an analog signal when a photoacoustic wave is received.

The signal collection unit 140 converts the analog signal output from the receiving unit 120 into a digital signal and outputs the digital signal to the computer 150. The computer 150 stores the digital signal output from the signal collection unit 140 as signal data derived from an ultrasonic wave or a photoacoustic wave.

The computer 150 performs signal processing on the stored digital signal, thereby generating image data representing a photoacoustic image. Further, the computer 150 performs image processing on the obtained image data, and then outputs the image data to the display unit 160. The display unit 160 displays a photoacoustic image. A doctor, a technician, or the like as an operator can perform diagnosis by checking the photoacoustic image displayed on the display unit 160. The display image is stored in a memory in the computer 150, a data management system connected to the modality with a network, or the like, based on a storage instruction from the operator or the computer 150.

The computer 150 also performs drive control of components included in the photoacoustic apparatus. In addition to the image generated by the computer 150, the display unit 160 may display a graphical user interface (GUI) or the like. The input unit 170 is configured such that an operator can input information. By using the input unit 170, the operator can perform operations such as start and end of measurement, issuance of an instruction to save a created image, and the like.

The photoacoustic image obtained by the photoacoustic apparatus according to the present exemplary embodiment is a conception including all images derived from photoacoustic waves generated by light irradiation. The photoacoustic image is image data representing at least one spatial distribution such as a generated sound pressure (initial sound pressure) of a photoacoustic wave, a light absorption energy density, and an optical absorption coefficient.

Hereinafter, each configuration of the photoacoustic apparatus according to the present exemplary embodiment will be described in detail.

(Light Irradiation Unit 110)

The light irradiation unit 110 includes a light source that emits pulsed light and an optical system that guides the pulsed light emitted from the light source to the object 100. The pulsed light includes light such as a so-called rectangular wave, a triangular wave, or the like.

The pulse width of the light emitted from the light source may be 1 ns or more and 100 ns or less. In addition, the wavelength of the light may be in the range of about 400 nm to 1600 nm. In the case of imaging a blood vessel with high resolution, a wavelength (400 nm or more and 700 nm or less) showing a high absorption coefficient in blood vessels may be used. In the case of imaging a deep part of a living body, light with a wavelength (700 nm or more and 1100 nm or less) which typically shows low absorption in a living background tissue (water, fat, or the like) may be used.

As a light source, a laser or a light emitting diode can be used. Furthermore, when measurement is performed using light of a plurality of wavelengths, a light source capable of transforming a wavelength may be used. When irradiating an object with light beams having a plurality of wavelengths, the plurality of light sources that generate light beams having mutually different wavelengths is prepared and light irradiation from respective light sources may be alternately carried out. Even when a plurality of light sources is used, they are collectively expressed as a light source. As the laser, various lasers such as a solid-state laser, a gas laser, a dye laser, and a semiconductor laser can be used. For example, a pulse laser such as a Nd:yttrium aluminum garnet (YAG) laser or an alexandrite laser may be used as a light source. Furthermore, a Ti:sa laser or an optical parametric oscillators (OPO) laser using Nd:YAG laser light as excitation light may be used as the light source. Furthermore, a microwave source may be used as a light source.

An optical element such as a lens, mirror, and optical fiber can be used for an optical system. In a case where the object 100 is a breast, in order to widen the beam diameter of the pulsed light for irradiation, the light emitting portion of the optical system may include a diffusion plate or the like for diffusing light. On the other hand, in a photoacoustic microscope, in order to increase the resolution, the light emitting portion of the optical system may include a lens or the like, and the beam may be focused to perform irradiation.

The light irradiation unit 110 may directly irradiate the object 100 with the pulsed light from the light source instead of provide the optical system.

(Receiving Unit 120)

The receiving unit 120 includes a transducer 121 that outputs an electric signal when an acoustic wave is received, and a support 122 that supports the transducer 121. In addition, the transducer 121 can also transmit acoustic waves. For convenience sake, only one transducer 121 is illustrated in FIG. 2, but the receiving unit 120 may include the plurality of transducers.

As a member constituting the transducer 121, a piezoelectric ceramic material typified by piezoelectric zirconate titanate (PZT) and a polymer piezoelectric film material typified by polyvinylidene fluoride (PVDF) can be used. Furthermore, elements other than the piezoelectric element may be used. For example, a capacitive micro-machined ultrasonic transducer (CMUT), and a transducer using a Fabry-Perot interferometer can be used. Any transducer may be adopted as long as the transducer can output an electric signal when an acoustic wave is received. Furthermore, the signal obtained by the transducer is a time-split signal. That is, the amplitude of the signal obtained by the transducer represents a value (for example, a value proportional to a sound pressure) based on a sound pressure received by the transducer at each time.

Typically, the frequency components constituting the photoacoustic wave are 100 KHz to 100 MHz, and the transducer 121 is adopted which can detect these frequencies.

The support 122 may include a metal material or the like having high mechanical strength. In order to cause a large amount of irradiation light to enter the object, a process of mirror finishing or light scattering may be performed on the surface of the support 122 on the object 100 side. In the present exemplary embodiment, the support 122 has a hemispherical shell shape and is configured to support the plurality of transducers 121 on a hemispherical shell. In this case, the directional axis of the transducer 121 disposed on the support 122 gathers near the curvature center of a hemisphere. When images are generated using the signals output from the plurality of transducers 121, an image near the center of curvature has a high quality. The support 122 may have any configuration as long as the support 122 can support the transducer 121. The support 122 may be arranged in such a manner that a plurality of transducers is juxtaposed in a plane or curved surface referred to as 1D array, 1.5D array, 1.75D array, and 2D array.

Furthermore, the support 122 may function as a container for retaining the acoustic matching material. That is, the support 122 may be a container for arranging the acoustic matching material between the transducer 121 and the object 100.

In addition, the receiving unit 120 may include an amplification unit that amplifies a time-series analog signal output from the transducer 121. Furthermore, the receiving unit 120 may include an A/D converter that converts the time-series analog signal output from the transducer 121 into a time-series digital signal. In other words, the receiving unit 120 may include a signal collection unit 140 to be described below.

In order to detect the acoustic wave at various angles, the transducer 121 may ideally be arranged so as to surround the object 100 from the entire circumference. However, when the transducer cannot be placed in such a manner that the object 100 is surrounded over the entire circumference, as illustrated in FIG. 2, the transducer may be placed on the hemispherical support 122 so as to nearly surround the entire circumference. Although only one transducer 121 is illustrated in FIG. 2, a plurality of transducers may be arranged on the support 122 on the hemisphere.

The arrangement and number of transducers and the shape of the support may be optimized according to the object, and any receiving unit 120 can be employed in the present invention.

A space between the receiving unit 120 and the object 100 is filled with a medium through which a photoacoustic wave can propagate. As the medium, a material is adopted through which an acoustic wave can propagate, has a matched acoustic characteristic at the interface with the object 100 and the transducer 121, and has as high transmittance as possible for the photoacoustic wave. For example, water, or ultrasonic gel can be adopted as this medium.

(Driving Unit 130)

The driving unit 130 changes the relative position between the object 100 and the receiving unit 120. In the present exemplary embodiment, the driving unit 130 is a device that moves the support 122 in an XY direction, and is an electric-powered XY stage equipped with a stepping motor. The driving unit 130 includes a motor such as a stepping motor that generates driving force, a driving mechanism that transmits driving force, and a position sensor that detects position information of the receiving unit 120. As the driving mechanism, a lead screw mechanism, a link mechanism, a gear mechanism, or a hydraulic mechanism can be used. As the position sensor, a potentiometer using an encoder, a variable resistor, or the like can be used.

The driving unit 130 is not limited to a type which changes the relative position between the object 100 and the receiving unit 120 in the XY directions (two dimensions), and may be changed to a type which drives in one dimension or three dimensions.

In order to change the relative position between the object 100 and the receiving unit 120, the driving unit 130 may fix the receiving unit 120 and move the object 100. In the case of moving the object 100, it is conceivable to move the object 100 by moving an object supporting unit (not illustrated) that supports the object 100. Alternatively, both the object 100 and the receiving unit 120 may be moved.

Further, the driving unit 130 may move the relative position continuously or may move by a step-and-repeat operation. The driving unit 130 may be an electric-powered stage or a manual stage.

Furthermore, in the present exemplary embodiment, the driving unit 130 drives simultaneously the light irradiation unit 110 and the receiving unit 120 to perform scanning; however, the driving unit 130 may drive only the light irradiation unit 110 or may drive only the receiving unit 120.

(Signal Collection Unit 140)

The signal collection unit 140 includes an amplifier that amplifies an electric signal that is an analog signal output from the transducer 121, and an A/D converter that converts an analog signal output from the amplifier into a digital signal. The signal collection unit 140 may include a field programmable gate array (FPGA) chip. The digital signal output from the signal collection unit 140 is stored in a storage unit 152 in the computer 150. The signal collection unit 140 is also referred to as a data acquisition system (DAS). In the present specification, an electric signal is a conception including both an analog signal and a digital signal. The signal collection unit 140 is connected to a light detection sensor attached to a light emission unit of the light irradiation unit 110, and may start processing in synchronization with the pulsed light which the light irradiation unit 110 has emitted as a trigger. In addition, the signal collection unit 140 may start the processing in synchronization with an instruction issued using a freeze button or the like as a trigger.

(Computer 150)

The computer 150 includes an arithmetic unit 151, a storage unit 152, and a control unit 153. The function of each component will be described in describing a processing flow.

A unit that is the arithmetic unit 151 and has an arithmetic function may include a processor such as a central processing unit (CPU) or a graphics processing unit (GPU), or an arithmetic circuit such as an FPGA chip. These units may include not only a single processor or an arithmetic circuit but also a plurality of processors and arithmetic circuits. The arithmetic unit 151 may process the received signal upon receipt of various parameters such as a sound speed in the object and the configuration of a holding cup from the input unit 170.

The storage unit 152 may include a read only memory (ROM), and a non-temporary storage medium such as a magnetic disk or a flash memory. Furthermore, the storage unit 152 may be a volatile medium such as a random access memory (RAM). The storage medium in which the program is stored is a non-transitory storage medium. The storage unit 152 may include only one storage medium or a plurality of storage media.

The storage unit 152 can store image data indicating the photoacoustic image generated by the arithmetic unit 151 by the method described below.

The control unit 153 includes an arithmetic element such as a CPU. The control unit 153 controls operation of each component of the photoacoustic apparatus. The control unit 153 may control each component of the photoacoustic apparatus in response to an instruction signal issued via various operations such as start of measurement instructed from the input unit 170. Furthermore, the control unit 153 reads out the program code stored in the storage unit 152 and controls the operation of each component of the photoacoustic apparatus.

The computer 150 may be a specially designed workstation. In addition, each component of the computer 150 may include different hardware. Further, at least a part of the components of the computer 150 may be configured of a single hardware device.

Figure 3:
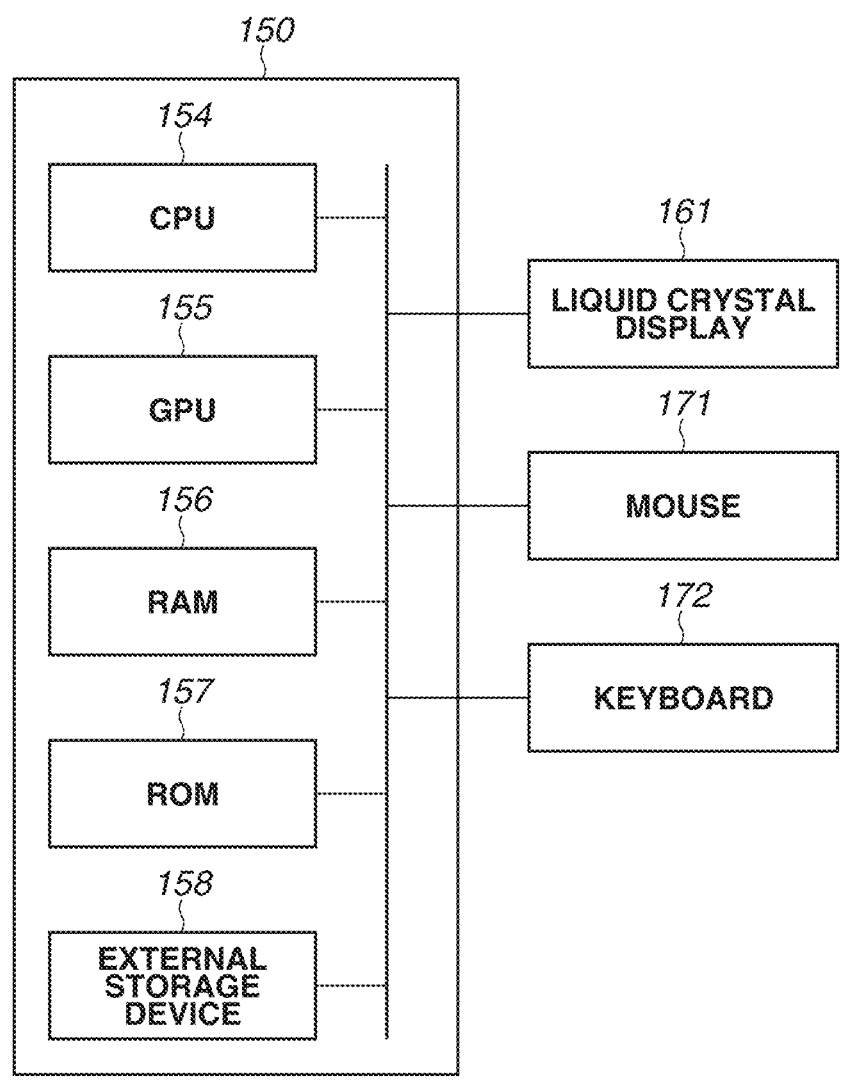
FIG. 3 is a configuration diagram of computer and peripheral equipment of the computer according to the first exemplary embodiment.

FIG. 3 illustrates a specific configuration example of the computer 150 according to the present exemplary embodiment. The computer 150 according to the present exemplary embodiment includes a CPU 154, a GPU 155, a RAM 156, a ROM 157, and an external storage device 158. Furthermore, a liquid crystal display 161 as a display unit 160, a mouse 171 as an input unit 170, and a keyboard 172 are connected to the computer 150.

In addition, the computer 150 and the plurality of transducers 121 may be placed in a common housing. However, a part of the signal processing may be performed by a computer placed in the housing, and the remaining signal processing may be performed by a computer provided outside the housing. In this case, computers provided inside and outside the housing can be collectively referred to as a computer according to the present exemplary embodiment. In other words, the hardware constituting the computer need not be placed in one housing.

(Display Unit 160)

The display unit 160 is a display such as a liquid crystal display or organic electroluminescence (EL). The display unit 160 is a device displaying an image based on object information obtained by the computer 150, numerical values of specific positions, and the like. The display unit 160 may display a GUI for operating an image and a device. When information about the object is displayed, it is also possible to perform image processing (adjustment of luminance value, or the like) on the display unit 160 or the computer 150 and display the object information.

(Input Unit 170)

As the input unit 170, an operation console that can be operated by a user and is configured of a mouse, a keyboard, or the like can be adopted. What can be input may be selection of a condition of image reconstruction, a method of positional deviation correction, an interpolation method, or the like. Further, a weight may be changed and added to a positional deviation amount by a slider bar while checking the synthesized image. Furthermore, the display unit 160 may include a touch panel, and the display unit 160 may be used as the input unit 170.

Each component of the photoacoustic apparatus may be configured to be separated from each other, or configured as one integrated apparatus. Further, at least a part of the components of the photoacoustic apparatus may be configured as one integrated apparatus.

(Object 100)

While the object 100 does not constitute a photoacoustic apparatus, it will be described below. The photoacoustic apparatus according to the present exemplary embodiment can be used for the purpose of diagnosis of malignant tumor and the vascular disease of a human and animal and follow-up observation of chemotherapy. Therefore, as the object 100, a living body is assumed. More specifically, as a diagnosis target body part a breast of human body and animal, each organ, vascular network, head, neck, and abdomen portion, limb including fingers and toes, and the like are assumed. For example, if the human body is an object to be measured, oxygen oxyhemoglobin or deoxyhemoglobin, blood vessels containing many thereof or new blood vessels formed in the vicinity of the tumor may be the object of an optical absorber. Plaque of the carotid artery wall or the like may be used as the object of the optical absorber. Dyes such as methylene blue (MB) and indocyanine green (ICG), gold microparticles, or an accumulated or chemically modified one of these materials which are introduced from the outside may be used as the optical absorber.

Figure 4:
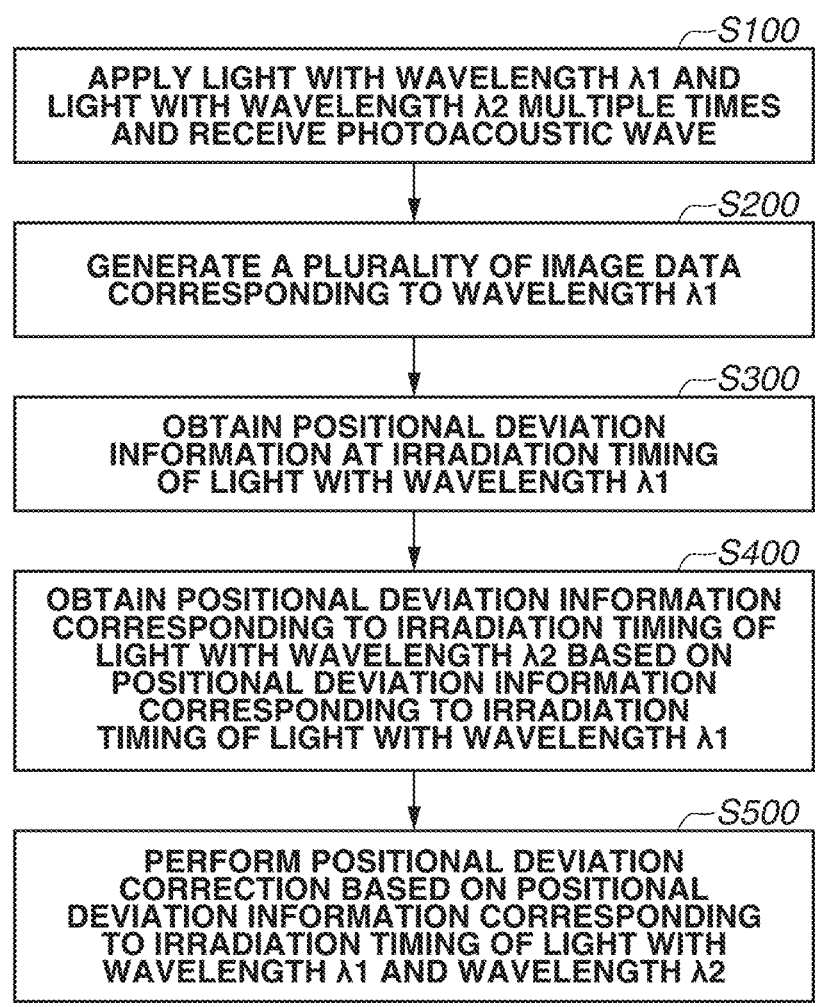
FIG. 4 is a flow chart illustrating an operation of the photoacoustic apparatus according to the first exemplary embodiment.

The operation of the photoacoustic apparatus including information processing according to the present exemplary embodiment will be described below along a flow chart illustrated in FIG. 4.

(Step S100: Step of Applying Light with Wavelength λ1 and Light with Wavelength λ2 a Plurality of Times and Receiving Photoacoustic Wave)

The light irradiation unit 110 irradiates the object 100 with light of a wavelength λ1 and light of a wavelength λ2 different from the wavelength λ1 a plurality of times respectively, and the receiving unit 120 receives the photoacoustic wave generated by light irradiation. The control unit 153 transmits scanning information and information (control signal) indicating light irradiation to the probe 180. While the driving unit 130 moves the receiving unit 120, the light irradiation unit 110 irradiates the object 100 with pulsed light of a plurality of wavelengths a plurality of times. That is, during a period in which light irradiation is performed a plurality of times, the driving unit 130 moves the receiving unit 120. As a result, the driving unit 130 can move the receiving unit 120 so that the receiving unit 120 is located at different positions at the time of light irradiation. The transducer 121 outputs a signal corresponding to the number of times of light irradiation when the photoacoustic wave generated by the light irradiation unit 110 which applies the pulsed light a plurality of times, is received. Hereinafter, the signals output in plural irradiations with light of a plurality of wavelengths are collectively referred to as a signal group corresponding to the plurality of wavelengths.

Hereinafter, a case where light irradiation is performed N times will be described. The signal obtained by the i-th light irradiation at the wavelength λ1 is represented by $$S_{\lambda 1, i} \ (1 \leq i \leq N) \qquad \text{Expression 1.}$$

An item with subscript "i" indicates that the item corresponds to i-th light irradiation. "i" is a positive integer and is also referred to as a pulse index.

Figure 5:
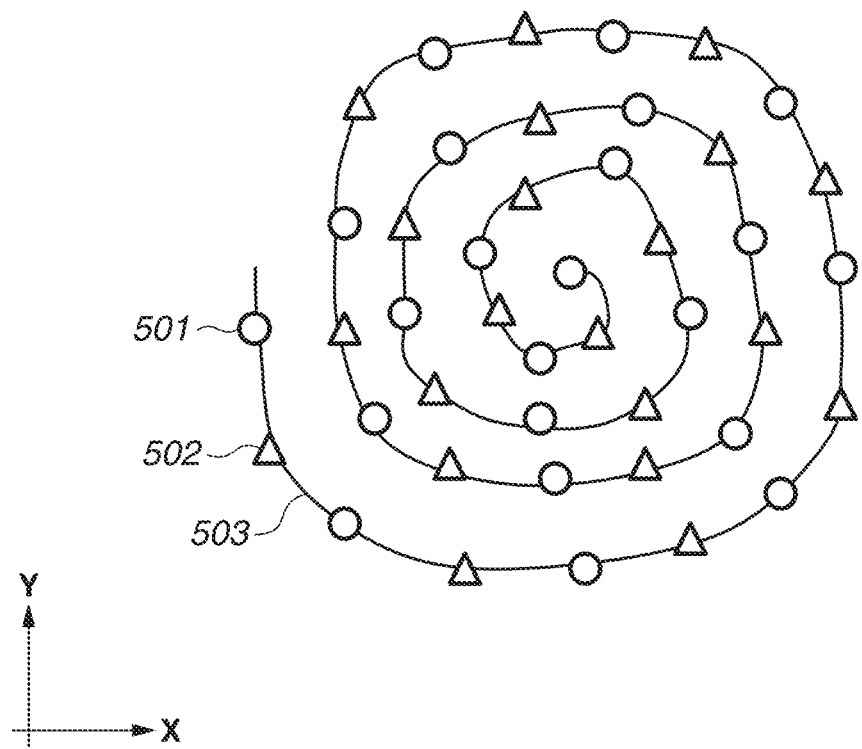
FIG. 5 is a schematic diagram illustrating a measurement position of the photoacoustic apparatus according to the first exemplary embodiment.

For example, as illustrated in FIG. 5, light irradiation and photoacoustic wave reception can be performed while moving the probe 180. A circle indicated by reference numeral 501 represents a position (measurement position) of the probe 180 when irradiated with the light of the wavelength λ1. A triangle indicated by reference numeral 502 represents a position (measurement position) of the probe 180 when irradiated with the light of the wavelength λ2. A solid line denoted by reference numeral 503 represents a trajectory of the probe 180. As illustrated in FIG. 5, in the present exemplary embodiment, the driving unit 130 may move the probe 180 while the light irradiation unit 110 alternately applies light of a plurality of wavelengths. In the example illustrated in FIG. 5, the probe 180 is scanned spirally inward from the outermost locus. In FIG. 5, the diagram is shown in an XY plane for the sake of convenience; however, the probe may be scanned three-dimensionally instead of in a plane.

The signal collection unit 140 performs analog-digital (AD) conversion processing and the like on a signal group corresponding to a plurality of wavelengths, which is an analog signal group output from the transducer 121, and transmits the processed photoacoustic signal to the computer 150. The photoacoustic signal as a digital signal group is stored in the storage unit 152.

(Step S200: Step of Obtaining Image Data Group Corresponding to Wavelength $\lambda 1$)

The arithmetic unit 151 obtains an image data group corresponding to the light irradiation of the first wavelength based on the signal group obtained in step S100. The arithmetic unit 151 may generate image data from each signal of the light irradiation to obtain image data obtained by light irradiation of wavelength $\lambda 1$ from among the generated image data. The arithmetic unit 151 may selectively use a signal corresponding to light irradiation with the wavelength $\lambda 1$ from the signal group to obtain image data obtained by light irradiation of the wavelength $\lambda 1$.

The arithmetic unit 151 generates a photoacoustic image by performing reconstruction processing such as universal back-projection (UBP) on the photoacoustic signal. When the photoacoustic image is generated, the photoacoustic signal stored in the storage unit 152 may be deleted. Image data obtained by one time pulsed light irradiation is referred to also as pulse volume data. The pulse volume data is obtained in the form of volume data in which the values at the relevant position are stored in each of voxels arranged in two or three dimensions (also referred to as pixels in the case of two dimensions). Volume data can be referred to also as two or three dimensional volume, two or three dimensional image, and two or three dimensional tomogram.

Regarding the reconstruction method, known reconstruction methods such as time domain reconstruction method, Fourier domain reconstruction method, model-based reconstruction method (iterative reconstruction method), and the like can be adopted. For example, a time domain reconstruction technique called Universal Back-Projection (UBP) as described in PHYSICAL REVIEW E71, 016706 (2005) can be adopted.

The arithmetic unit 151 may obtain initial sound pressure distribution data $$P_{\lambda a, i} \ (1 \leq a \leq L, 1 \leq i \leq N) \qquad \text{Expression 2.}$$

"a" is a wavelength index indicating that "a" is an item corresponding to light irradiation with wavelength $\lambda a$. The arithmetic unit 151 may obtain the initial sound pressure distribution data based on the position information of the transducer at the time of light irradiation in addition to the signal group. The arithmetic unit 151 can obtain the position information by reading the position information of the transducer at the time of each light irradiation. The position information is stored in the storage unit 152 in advance. In addition, the arithmetic unit 151 may obtain the position information of the transducer by receiving the position information of the receiving unit 120 from the position sensor provided in the driving unit 130 with light irradiation as a trigger.

Figure 6:
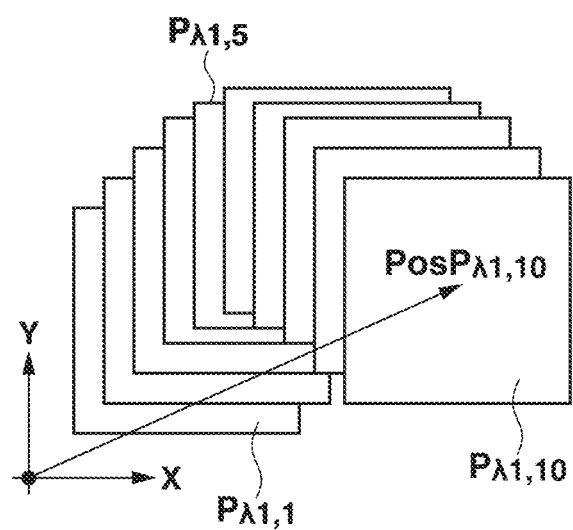
FIG. 6 is a schematic diagram illustrating pulse volume data according to the first exemplary embodiment.

FIG. 6 illustrates a part ($P_{\lambda 1, 1}$ to $P_{\lambda 1, 10}$) of the pulse volume data at the wavelength $\lambda 1$ according to the present exemplary embodiment. Pulse volume data in the present exemplary embodiment is volume data in three-dimensional space, but pulse volume data is represented in an XY plane for the sake of explanation of space. In the present exemplary embodiment, the reconstruction region is set such that at least a part of the temporally adjacent initial sound pressure distribution data is superimposed. In the present exemplary embodiment, a cubic region of 60 mm square centering on the center of curvature of the hemispherical support 122 is a reconstruction region to be reconstructed based on one-time light irradiation, that is, one electric signal group. In this case, the size (60 mm) of the region reconstructed by one-time light irradiation is larger than the movement amount of the receiving unit 120 during light irradiation. Therefore, as illustrated in FIG. 6, two or more pulse volume data corresponding to a temporally continuous light irradiation are superimposed. The size and shape of the reconstruction region may be preset. Further, the user may specify the size and shape of the reconstruction region using the input unit 170. The center position of each pulse volume data with respect to the reference position is set as the position of each pulse volume data. FIG. 6 illustrates, as an example, a position $PosP_{\lambda 1, 10}$ of pulse volume data $P_{\lambda 1, 10}$. In the example of FIG. 6, since the position of the receiving unit 120 is different in every light irradiation, the pulse volume data obtained in the present exemplary embodiment illustrated in FIG. 6 are located at different positions relative to the reference position.

In this step, the arithmetic unit 151 may obtain light fluence distribution data $\Phi$ [Pa·m3/J] within the object. Then, the arithmetic unit 151 may obtain the light absorption coefficient distribution data $\mu a$ [1/m] within the object by dividing the initial sound pressure distribution data by the light fluence distribution data and Grueneisen coefficient distribution data. In this case, the light absorption coefficient distribution data may be used as pulse volume data.

For example, as described in Proc. of SPIE Vol. 7561 756117-1, the arithmetic unit 151 may obtain the light fluence distribution data by solving a light diffusion equation.

Further, for example, it is known that Grueneisen coefficient is almost uniquely determined when the type of the object is determined; therefore, it is possible to previously store Grueneisen coefficient distribution data $\Gamma$ corresponding to the object in the storage unit 152. Then, the arithmetic unit 151 may read Grueneisen coefficient distribution data $\Gamma$ stored in advance in the storage unit 152 to obtain Grueneisen coefficient distribution data $\Gamma$.

The user may grip the probe 180 having a grip portion and move the probe 180. Besides, it is not necessary to move the probe 180 during a period in which light irradiation is performed a plurality of times. Further, the arithmetic unit 151 may obtain the image data of the entire imaging region based on an electric signal group obtained by one-time light irradiation, and repeat the obtaining when light irradiation is carried out a plurality of times.

(Step S300: Step of Obtaining Positional Deviation Information Corresponding to Timing of Irradiating with Light of Wavelength $\lambda 1$)

Based on the image data group corresponding to the wavelength $\lambda 1$ obtained in step S200, the arithmetic unit 151 obtains positional deviation information corresponding to the timing of irradiating with the light of the wavelength $\lambda 1$. For example, as described below, by calculating the positional deviation amount between the pulse volume data and calculating the positional deviation amount of the volume data in which the pulse volume data are synthesized, it is possible to obtain the positional deviation information.

First, the arithmetic unit 151 estimates the positional deviation amount of each pulse volume data due to a variation in the relative positional relationship between the object and the receiving unit during light irradiation with the wavelength λ1. At that time, a pair of arbitrary pulse volume data is selected from the obtained pulse volume data. The k-th pair is denoted as R_k. Further, one of the pulse volume data of the wavelength λ1 constituting the pair R_k is denoted as $P_{\lambda 1, k1}$, and the other is denoted as $P_{\lambda 1, k2}$. In the present exemplary embodiment, a case where K pairs are selected will be described below. It is preferable that two pulse volume data having an overlapping region are paired. This makes it possible to avoid comparing pulse volume data having no common feature with each other, so that redundant calculations can be reduced. Furthermore, it is preferable to pair the pulse volume data having a large overlapping region with each other. Therefore, for example, the arithmetic unit 151 may select a pair in which the ratio of the volume of the overlapping region between pulse volume data is equal to or greater than a predetermined value. Further, as will be described below, when synthesized volume data is used for positional deviation correction, pairs in which regions having a large number of superimposed pulse volume data overlap with each other may be selected.

Further, with respect to certain pulse volume data, pulse volume data whose index is included within a predetermined range may be selected as an object of a pair from the index of the pulse volume data. Further, pulse volume data which have consecutive indexes, that is, pulse volume data which are continuous in time may be selected as a pair target. For example, in the present exemplary embodiment, the arithmetic unit 151 selects a pair for pulse volume data whose overlapping region is 50% or more.

Hereinafter, an example of a method for estimating the positional deviation amount of each pulse volume data will be described.

The arithmetic unit 151 obtains a similarity function F_k between $P_{\lambda 1, k1}$ and $P_{\lambda 1, k2}$, as illustrated in Expression 3.

$$F\_k(x,y,z) = f_{simil}(P\_k, x, y, z) \quad \text{Expression 3}$$

Here, the similarity function F_k is a function for calculating similarity when the relative position of one pulse volume data $P_{\lambda 1, k2}$ with respect to the other pulse volume data $P_{\lambda 1, k1}$ constituting the pair R_k is translated by (x,y,z). Here, the function fsimil returns a high value as a function value when the similarity between images is high. Obtaining of the similarity function F means obtaining a function value when the relative position between image data is discretely changed by the translation amount (x,y,z) which is an argument of each function, that is, within a predetermined range. For example, the obtaining means obtains a set of (2L+1)×(2L+1)×(2L+1) values returned by F for each of cases where the values of x, y, and z are each changed as integer values from −L to +L. In a more advanced manner, from the set of (2L+1)×(2L+1)×(2L+1) values, a similarity function F may be derived and obtained as information closer to a continuous function by additionally using a bilinear method, a bicubic method, or the like.

Furthermore, a function value can be obtained in a case where the positions of $P_{\lambda 1, k2}$ are discretely changed within a predetermined range with reference to a position translated by a relative position of $P_{\lambda 1, k2}$ with respect to $P_{\lambda 1, k1}$ (movement amount of the receiving unit 120 during light irradiation).

For example, as a function for calculating similarity, an arbitrary degree of similarity measure such as sum of squared difference (SSD), sum of absolute difference (SAD), mutual information amount, mutual correlation and the like can be applied. Further, for example, a similarity function can be obtained by extracting characteristic forms from the pulse volume data and measuring the degree of matching with those positions. As a feature to be extracted, a feature extracted by known techniques commonly used in image processing fields such as an anatomical feature about a blood vessel, edge detection and corner detection may be used. As a feature to be extracted, a higher-order local image feature such as a scale-invariant feature transform (SIFT) feature and a speeded up robust feature (SURF) feature generally used in technical fields such as computer vision may be used. According to these methods, it is considered that a more robust similarity function can be obtained by the difference in luminance distribution between pulsed volume data, and the mixing of noise.

The arithmetic unit 151 may also obtain the similarity function by multiplying the result of the similarity calculation by a weight.

Furthermore, when the degree of similarity cannot be calculated correctly between the pulse volume data which is subjected to the similarity calculation, the result may not be used for subsequent processing. As a case where the degree of similarity cannot be calculated correctly, it is conceivable that the degree of similarity is substantially small or does not change regardless of the translation to any of them. According to this processing, the comparison result (similarity function) between the pulse volume data in which the same characteristic is sufficiently exhibited can be selectively used for subsequent processing.

Subsequently, as illustrated in Expression 4, the arithmetic unit 151 obtains a translation amount M_k that maximizes the function value of the similarity function F_k.

$$M\_k = \arg\max(F\_k(x,y,z)) \quad \text{Expression 4}$$

The arithmetic unit 151 obtains the translation amount M_k that maximizes the function value of the similarity function F_k for each pair.

When estimating the position of the pulse volume data, an evaluation function that keeps the translation amount M_k, which is an individual optimal value for pair R_k, as much as possible, is defined. More specifically, an evaluation function is defined in which the value decreases as the positions of $P_{\lambda 1, k2}$ with respect to $P_{\lambda 1, k1}$ move away from the translation amount M_k. Expression 5 represents an example of the evaluation function E_k in this case.

$$E\_k = (M\_k - (PosP_{\lambda 1, k1} - PosP_{\lambda 1, k2})^2) = (M\_k(x) - (PosP_{\lambda 1, k1(x)} - PosP_{\lambda 1, k2(x)})^2) + (M\_k(y) - (PosP_{\lambda 1, k1(y)} - PosP_{\lambda 1, k2(y)})^2) + (M\_k(z) - (PosP_{\lambda 1, k1(z)} - PosP_{\lambda 1, k2(z)})^2) \quad \text{Expression 5}$$

$PosP_{\lambda 1, k1}$ represents the position of $P_{\lambda 1, k1}$ with respect to the reference position. $PosP_{\lambda 1, k2}$ represents the position of $P_{\lambda 1, k2}$ with respect to the reference position. When defining the evaluation function, the similarity function F_k may be approximated to a quadratic function that fits the similarity function F_k. Furthermore, in a case where the similarity function F_k can be approximated in such a way that it decreases according to a quadratic function around the translation amount M_k, Expression 3 becomes a function that makes the value of the similarity function F_k approximate around the translation amount M_k from the positional relationship between $P_{\lambda 1, k1}$ and $P_{\lambda 1, k2}$.

Subsequently, the arithmetic unit 151 obtains a position $PosP'_{\lambda 1, j}$ of all the pulse volume data with respect to the reference position when a cost function E defined as Expression 6 is minimized. Where "j" is a pulse index for a pulse.

$$E = \sum_{k=1}^{K} E\_k$$

$$= \sum_{k=1}^{K} (M\_k - (PosP_{\lambda1,k1} - PosP_{\lambda1,k2})^2)$$

$$= \sum_{k=1}^{K} \{(M\_k(x) - (PosP_{\lambda1,k1(x)} - PosP_{\lambda1,k2(x)})^2) +$$

$$(M\_k(y) - (PosP_{\lambda1,k1(y)} - PosP_{\lambda1,k2(y)})^2) +$$

$$(M\_k(z) - (PosP_{\lambda1,k1(z)} - PosP_{\lambda1,k2(z)})^2)\}$$

Expression 6

The position of the pulse volume data with respect to the reference position when the cost function is minimized, represents the position information of the pulse volume data after the position deviates due to a variation in the relative positional relationship between the object 100 and the receiving unit 120.

For example, the arithmetic unit 151 obtains a solution that minimizes (comes closest to 0) the cost function E illustrated in Expression 4 by solving a linear least squares method. As a result, since the position $PosP'_{\lambda1,j}$ of each pulse volume data can be uniquely determined, the calculation cost is small.

Instead of the optimization of the cost function by the linear optimization described above, any known method can be used for optimizing the cost function. For example, optimization of the cost function may be performed by a nonlinear optimization method such as a steepest descent method or a Newton method by repeated calculation. More specifically, the arithmetic unit 151 searches for the position of each pulse volume data which minimizes the cost function to obtain position information after a position of the pulse volume data deviates with respect to the reference position.

The cost function may be defined in such a way that regularization is applied to a variation (movement) between light irradiation at each position of assumed pulse volume data. When a breast is an object, it is thought that movement by respiration is dominant. In this case, it is thought that the movement of the object is a movement of about several mm at the maximum, and the movement thereof is temporally continuous and smooth. Further, it is thought that the movement is periodic. Regularization can be applied in such a way that suppression can be exerted to prevent calculation of a movement that deviates from the assumed object movement as described above.

Regularization can be applied in any way. For example, regularization can be performed by multiplying the sum of the variation amounts (moving distances) of the object in derivation processing by a predetermined weighting coefficient and adding the resultant value to the cost function. Alternatively, a value calculated based on the frequency component value of the variation of the object may be added to the cost function. Alternatively, a method of typical variation of the object may be prepared as a model, and a difference from the variation in the model may be added as a cost to the cost function.

Furthermore, "to minimize the cost function" includes not only a case where the cost function is definitely minimized, but also a case where the value of the cost function becomes less than a predetermined value when the solution candidate varies or a case where the variation amount of the cost function is equal to or less than the predetermined value. In other words, the arithmetic unit 151 may determine that the cost function has been minimized when the cost function satisfies a predetermined condition. Alternatively, the user may use the input unit 170 to give an indication that the cost function has been minimized. In this case, the arithmetic unit 151 determines that the cost function has been minimized in response to the indication from the input unit 170.

Subsequently, the arithmetic unit 151 obtains the positional deviation amount $Mopt_{\lambda1,j}$ when the cost function is minimized with respect to each pulse volume data. This positional deviation amount $Mopt_{\lambda1,j}$ represents the positional deviation amount of each pulse volume data due to a variation in the relative positional relationship between the object 100 and the receiving unit 120.

Figure 7:
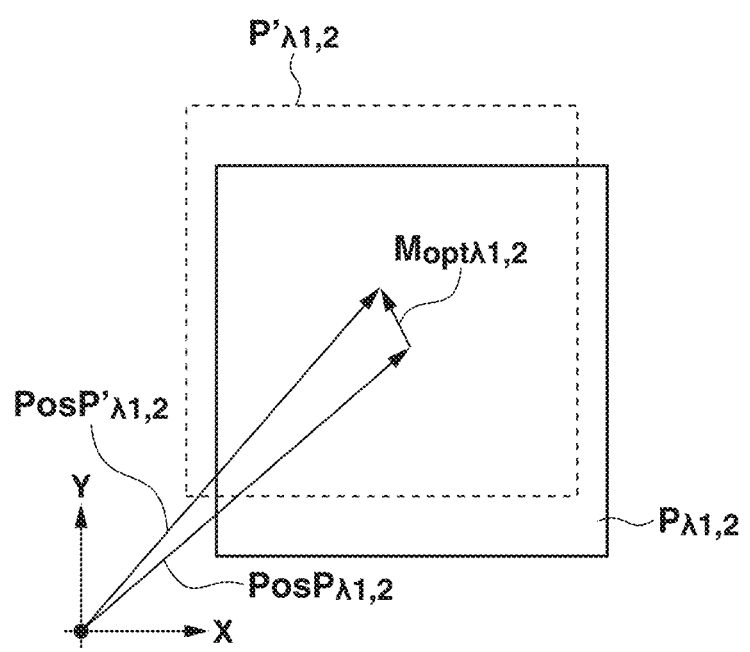
FIG. 7 is a schematic diagram illustrating a positional deviation amount between images according to the first exemplary embodiment.

FIG. 7 illustrates a position $PosP_{\lambda1,2}$ of the pulse volume data $P_{\lambda1,2}$ and a position $PosP'_{\lambda1,2}$ of the pulse volume data $P'_{\lambda1,2}$ when the cost function is minimized by the above method. In FIG. 7, the pulse volume data $P_{\lambda1,2}$ is represented by a solid line, and the pulse volume data $P'_{\lambda1,2}$ when the cost function is minimized is represented by a broken line.

In this step, any method may be used as long as positional deviation information of the pulse volume data due to the variation in the relative position between the object 100 and the receiving unit 120 can be obtained.

Alternatively, the arithmetic unit 151 may obtain the positional deviation information by using the k-th synthesized volume data $G_{\lambda1,k}$ at the wavelength $\lambda1$ obtained by synthesizing two or more pulse volume data. At that time, a rectangular region including all synthesized pulse volume data and having a minimum value may be used as synthesized volume data, or an arbitrary region including a region where at least two or more pulse volume data are superimposed may be used as synthesized volume data. In other words, the region of the synthesized volume data does not need to include all the pulse volume data to be synthesized.

The synthesized volume data is obtained by adding the selected pulse volume data according to the position. Alternatively, the pulse volume data may be averaged by adding the selected pulse volume data and dividing by the number of overlapping pulse volumes, or any method can be used as long as volume data that more accurately reproduces the features of the object can be obtained. However, the processing of correcting the variation of the relative position between the object 100 and the receiving unit 120 during light irradiation (for example, the processing of changing the position of the pulse volume) is not included in "synthesis" according to this specification.

For example, the arithmetic unit 151 may perform synthesis by adding each of the pulse volume data to be synthesized after weighting each of the pulse volume data. Alternatively, the arithmetic unit 151 may calculate the additional value or the average value for the pulse volume data which excludes the value including many noises by using an outlier elimination method or the like.

Through these synthesis processing, noise included in each pulse volume data is reduced, so that synthesized volume data can be obtained that more accurately reproduces the features of the object. Further, when the number of synthesized volume data is smaller than the number of pulse volume data, it is possible to reduce the calculation amount and calculation cost by comparing the pulse volume data with each other, compared to the method for estimating the positional deviation of the entire pulse volume data.

However, the synthesized volume data obtained by synthesizing in this way includes the influence of the variation in the relative positional relationship between the object and the receiving unit of the photoacoustic wave in the multiple light irradiations. Therefore, there is a possibility that degradation in quality may be caused by the variation in the synthesized volume data. Hereinafter, in order to suppress the degradation of the quality, the processing of estimating the position of the pulse volume data from the estimated position of the synthesized volume data will be described.

The arithmetic unit 151 estimates a positional deviation amount $Mopt_{\lambda1,i}$ of each pulse volume data based on a positional deviation amount $MGopt_{\lambda1,j}$ of each synthesized volume data at the wavelength $\lambda1$.

The arithmetic unit 151 can allocate the positional deviation amount of the estimated synthesized volume data with respect to the positional deviation amount of the pulse volume data associated with the synthesized volume data. Regarding the positional deviation amount of other pulse volume data, the arithmetic unit 151 can perform estimation by performing interpolation processing on the positional deviation amount of the allocated pulse volume data. As a method of interpolation processing, known methods such as linear interpolation and spline interpolation can be adopted. In addition, interpolation processing may be performed by imposing a constraint in which a position that deviates from the expected movement of the object is not calculated.

Arbitrary pulse volume data among the pulse volume data to be synthesized may be the pulse volume data associated with the synthesized volume data. For example, when the pulse voltage data to be synthesized is an odd number, pulse volume data temporally located at the center may be associated with the synthesized volume data.

Furthermore, for example, when the pulse volume data to be synthesized is an even number as in the present exemplary embodiment, any one of the pulse volume data temporally located near the center may be associated with the synthesized volume data. For example, when ten pieces of pulse volume data are to be synthesized as in the present exemplary embodiment, the positional deviation amount $MGopt_{\lambda1,j}$ of the synthesized volume data $G_{\lambda1,j}$ at the wavelength $\lambda1$ may be assigned as the positional deviation amount $MGopt_{\lambda1},5j$ of the pulse volume data $P_{\lambda1,5j}$.

Furthermore, when the pulse voltage data to be synthesized is an even number, virtual pulse volume data temporally located at the center may be associated with the synthesized volume data. For example, when ten pieces of pulse volume data are to be synthesized as in the present exemplary embodiment, the positional deviation amount of the synthesized volume data $G_{\lambda1,j}$ at the wavelength $\lambda1$ may be assigned to the positional deviation amount of the virtual pulse volume data having the pulse index of 5.5j.

Further, when synthesized together with weighting, synthesis target pulse volume data weighted with the highest weight coefficient among pulse volume data may be associated with the synthesized volume data. Furthermore, among pulse volume data to be synthesized, pulse volume data having a median weighting coefficient may be associated with the synthesized volume data.

By the above processing, based on the positional deviation information of the synthesized volume data corresponding to the wavelength $\lambda1$, it is possible to obtain positional deviation information of the pulse volume data corresponding to the wavelength $\lambda1$. In this way, positional deviation information corresponding to timing of irradiating with the light of the wavelength $\lambda1$ may be obtained.

The positional deviation information may be obtained in the same manner as described above by using two-dimensional projection data such as a maximum intensity projection (MIP) of pulse volume data or synthesized volume data. Hereinafter, an example of the processing will be described.

The arithmetic unit 151 obtains MIP data as projection data projected in each of the X direction, the Y direction, and the Z direction with respect to the synthesized initial sound pressure distribution data $G_{\lambda1,j}$ at the wavelength $\lambda1$. The MIP data projected in the X direction is two-dimensional spatial information represented by Y axis and Z axis, and is denoted as $IG_{\lambda1,j}(y,z)$. The MIP data projected in the Y direction is two-dimensional spatial distribution information represented by the Z axis and the X axis, and is denoted as $IG_{\lambda1,j}(z,x)$. The MIP data projected in the Z direction is two-dimensional spatial distribution information represented by the X axis and the Y axis, and is denoted as $IG_{\lambda1,j}(x,y)$.

Note that as long as three-dimensional image data can be converted into two-dimensional image data, a projection method other than an MIP images may be adopted. For example, a minimum intensity projection (MINP) image may be generated and used in place of the MIP image. Alternatively, projection data may be obtained by adding a plurality of slides in the projection direction.

Subsequently, for each of the XY plane, the YZ plane, and the ZX plane, the relative position of one MIP data with respect to the other MIP data constituting the pair is translated to calculate the similarity. As the similarity calculation method, the above-described method can be used. For each of the XY plane, the YZ plane, and the ZX plane, the translation amounts MX_k, MY_k, and MZ_k at which the similarity of $P_{\lambda1,k2}$ with respect to $P_{\lambda1,k1}$ is the maximum and the average values of the components on the respective coordinate axes of the translation amounts are calculated as each component value of the three-dimensional translation amount M at which the similarity is maximized.

$$M\_k = \left(\frac{MY\_k + MZ\_k}{2}, \frac{MX\_k + MZ\_k}{2}, \frac{MX\_k + MY\_k}{2}\right) \quad \text{Expression 7}$$

The arithmetic unit 151 can estimate the position of each synthesized volume data when the cost function illustrated in Expression 4 is minimized, using the translation amount M_k illustrated in Expression 5.

With the above processing, the position of the synthesized volume data with respect to the reference position can be obtained based on the two-dimensional image data converted from the three-dimensional image data. By converting three-dimensional image data into two-dimensional image data, it is possible to obtain the position of the volume data after the position deviates, with less calculation cost as compared with the case where the processing is performed with the three-dimensional image data as it is.

Alternatively, by converting three-dimensional image data as the pulse volume into two-dimensional image data, the positional deviation information of the pulse volume data corresponding to the wavelength $\lambda1$ may be obtained by the above method. In this way, positional deviation information corresponding to the timing of irradiating with the light of the wavelength $\lambda1$ may be obtained.

Up to this point, a case has been described as an example in which translation occurs as a variation in the relative positional relationship between the object and the receiving unit. However, even in a case where rotation or deformation occurs as the variation, it is possible to estimate an amount of the positional deviation caused by the rotation or deformation.

For example, when rotation is taken into consideration, the arithmetic unit 151 can estimate the position and the rotation amount (positional deviation amount) of each pulse volume data using the rotation amount as an argument in addition to the translation amount. Subsequently, the arithmetic unit 151 can obtain synthesized volume data by performing rigid body conversion processing (positional deviation correction processing) on each pulse volume data based on the estimated position and rotation amount and then synthesizing the processed pulse volume data. Further, only the rotation amount may be the positional deviation amount, or a conversion matrix such as the calculated two-dimensional or three-dimensional translation/rotation matrix and various parameters for conversion may be treated as the positional deviation amount.

Furthermore, for example, in consideration of deformation, the arithmetic unit 151 can estimate a displacement amount using, as an argument, a displacement amount (at least one of translation and rotation amount) at each point set in the pulse volume data. Subsequently, the arithmetic unit 151 can obtain synthesized volume data by performing deformation processing (positional deviation correction processing) on each pulse volume data based on the estimated displacement amount and then synthesizing the processed pulse volume data. For example, the displacement amount between pulse volume data can be calculated by a method of expressing deformation such as free form deformation (FFD) or Thin Plate Spline. By the above-described processing, high-quality synthesized volume data can be obtained in consideration of higher order variation including deformation.

In the present exemplary embodiment, the obtaining of the pulse volume data is started after the measurement of the photoacoustic wave by the all light irradiation is completed. However, the pulse volume data may be sequentially obtained each time light irradiation is performed. In the latter case, the obtained pulse volume data may be sequentially displayed on the display unit 160. As a result, the user can confirm the obtained pulse volume data before all the measurements are completed. At this time, the region where the pulse volume data is superimposed may be synthesized by the above-described method.

Furthermore, in the present exemplary embodiment, the positional deviation amount is calculated after obtaining all the pulse volume data. However, the positional deviation amount may be sequentially calculated using pulse volume data obtained each time light irradiation is performed. Alternatively, a predetermined number of pulse volume data may be synthesized from sequentially obtained pulse volume data to generate synthesized volume data and sequentially calculate the positional deviation amount.

In addition, the volume data for calculating the positional deviation amount may be used after performing preliminary processing such as removing a negative value or normalizing the image intensity.

(Step S400: Step of Obtaining Positional Deviation Information Corresponding to Timing of Irradiating with Light of Wavelength λ2 Based on Positional Deviation Information Corresponding to Timing of Irradiating with Light of Wavelength λ1)

The arithmetic unit 151 obtains positional deviation information corresponding to timing of irradiating with light of wavelength λ2 based on positional deviation information corresponding to timing of irradiating with light of wavelength λ1 obtained in step S300. More specifically, from the positional deviation information corresponding to the specific wavelength calculated by the method described in step S300, the positional deviation information corresponding to other wavelengths is calculated. For example, when the timing of irradiation with the light is known, the positional deviation information corresponding to the timing of irradiation with the light of λ1 may be temporally interpolated. Furthermore, when the position of the probe 180 corresponding to the light irradiation timing, that is, the position of the receiving unit 120 is known, the positional deviation information corresponding to the irradiation timing of the light of the wavelength λ1 may be spatially interpolated. Through these interpolations, the arithmetic unit 151 may obtain positional deviation information corresponding to the irradiation timing of the light of the wavelength λ2.

Figure 8:
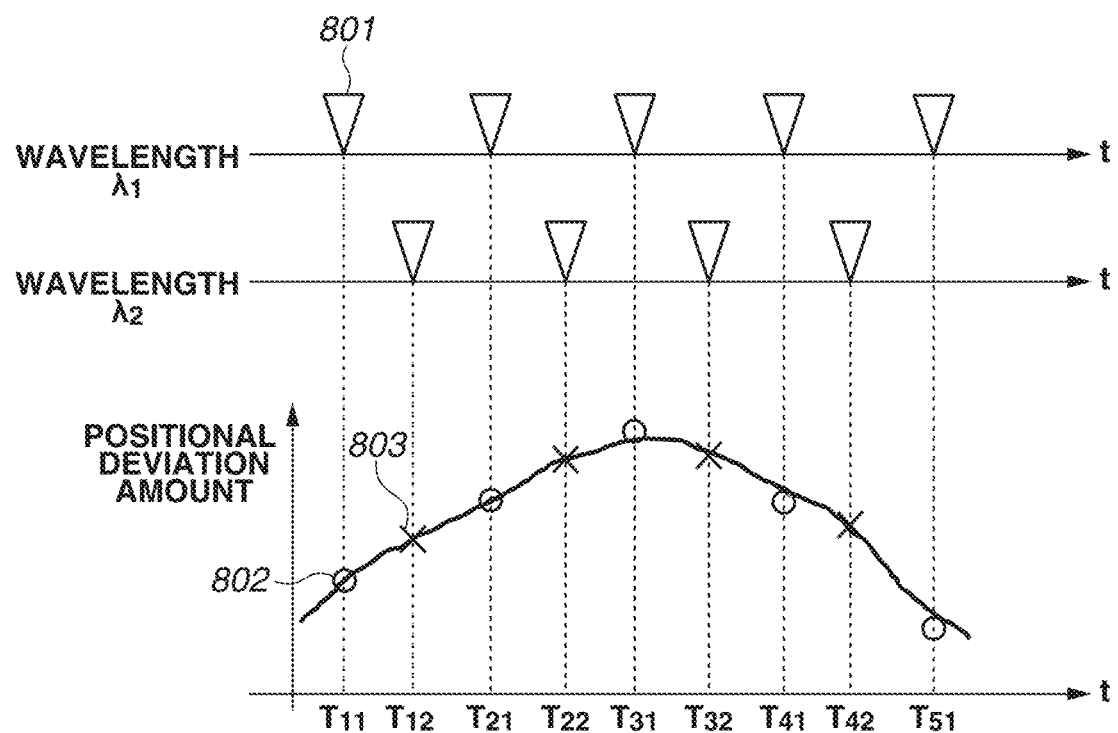
FIG. 8 is a sequence diagram for explaining a temporal interpolation of the positional deviation amount according to the first exemplary embodiment.

The case of calculating by temporal interpolation will be described with reference to FIG. 8. FIG. 8 includes a sequence diagram illustrating irradiation timing of pulsed light of a plurality of wavelengths at time t. FIG. 8 also includes a graph illustrating the positional deviation amount (translation amount) corresponding to each pulsed light at the wavelength λ1. The inverted triangle of reference numeral 801 schematically illustrates the irradiation timing of the pulsed light. It is understood that the pulsed light of wavelength λ1 is applied at times T11, T21, T31, T41, and T51, respectively. It is also understood that the pulsed light of wavelength λ2 is applied at times T12, T22, T32, T42, and T52, respectively. Furthermore, since the positional deviation amount corresponding to the irradiation timing of the pulsed light of the wavelength λ1 is calculated in step S300, the positional deviation amount is plotted with a circle 802 in FIG. 8. Therefore, the arithmetic unit 151 calculates the positional deviation amount corresponding to the wavelength λ2 by temporally interpolating from the positional deviation amount at the wavelength λ1. In FIG. 8, a cross mark 803 indicates the positional deviation amount corresponding to the irradiation timing of the pulsed light of the wavelength λ2 calculated by the temporal interpolation. Although it is ideally correct to use Lanczos interpolation as the interpolation method, any interpolation method such as linear interpolation, cubic interpolation, and spline interpolation may be used. Here, as an example, explanation will be made in the case of using linear interpolation and Lanczos interpolation. For example, when the movement of the object being observed is later than the pulse irradiation time (sampling time) of wavelength λ1, the positional deviation amount corresponding to the timing of T12 at the wavelength λ2 can be calculated from the positional deviation amount at T11 and T21 corresponding to the wavelength λ1. When the positional deviation amounts at T11 and T21 are M11 and M21 respectively, the positional deviation amount M12 at T12 may be calculated by the following Expression 8.

$$M_{12} = \frac{M_{11} \cdot (T_{21} - T_{12}) + M_{21} \cdot (T_{12} - T_{11})}{T_{21} - T_{11}} \quad \text{Expression 8}$$

Calculation has been performed using M11 and M21 to calculate the positional deviation amount M12 of the pulse at the time T12 of the wavelength λ2. However, depending on the interpolation method, it is also possible to use the positional deviation amount of the pulse which is temporally away. For example, it is known that Lanczos interpolation is a type of multivariate interpolation, and is used to improve the sampling rate of digital signals, and interpolation can be performed best in Lanczos interpolation. Lanczos interpolation for a one-dimensional signal is performed by Expression 10 using the Lanczos kernel L (t) of Expression 9.

$$L(t) = \text{sinc}(t)\text{sinc}\left(\frac{t}{a}\right) \quad \text{if} -a < t < a \quad \quad \text{Expression 9}$$
$$\phantom{L(t) =} 0 \quad \text{otherwise}$$

$$S(t) = \sum_{i=[t]-a+1}^{[t]+a} s_i L(t-i) \quad \quad \text{Expression 10}$$

Here, "t" is time, "a" is a positive integer that determines the kernel size, "si" is a sample of a one-dimensional signal for a positive integer i, "S(t)" is the interpolated value, and [ ] is a floor function. Unlike the case of linear interpolation, it is understood that interpolation is performed using not only the positional deviation amount of the two nearest neighboring pulses but also the positional deviation amount of a plurality of nearby pulses.

Accordingly, it is possible to calculate the positional deviation amount of pulses of other wavelengths from the positional deviation amount of pulses temporally close to one wavelength. In addition, it is unnecessary to perform positional deviation correction on a plurality of wavelengths in the course of the processing, so that the calculation time can also be shortened.

As an example of a method for performing temporal interpolation, a method for calculating one two-dimensional Affine transformation matrix by interpolating from two two-dimensional Affine transformation matrices will be described.

The corresponding pulse volume data is obtained from the signal obtained by applying the pulsed light of the wavelength λ1 out of the obtained signal group of the pulsed light with the plurality of wavelengths. From the obtained pulse volume data of wavelength λ1, positional deviation correction based on Affine conversion is performed to calculate the positional deviation amount at wavelength λ2. The positional deviation amount at the wavelength λ2 is calculated as an Affine transformation matrix with respect to the pulse volume data.

First, assume that there are two two-dimensional Affine transformation matrices A1 and A2. Here, A1 is a position deviation amount (Affine transformation matrix) between pulse volume data $P_{\lambda1,0}$ obtained by applying pulsed light of wavelength λ1 at time t1 and pulse volume data $P_{\lambda1,1}$ obtained by applying pulsed light of wavelength λ1 at the time of t1+Δ. Furthermore, A2 is a position deviation amount between pulse volume data $P_{\lambda1,1}$ obtained by applying pulsed light of wavelength λ1 at time t1+Δ and pulse volume data $P_{\lambda1,2}$ obtained by applying pulsed light of wavelength λ1 at the time of t1+2Δ.

In this case, desired Affine transformation matrix B is a position deviation amount between pulse volume data $P_{\lambda2,1/2}$ obtained by applying pulse of wavelength λ2 at time t1+Δ/2 and pulse volume data $P_{\lambda2,3/2}$ obtained by applying pulsed light of wavelength at the time of t1+3Δ/2.

A1 can be decomposed into a rotation component referred to as A1R and an expansion/reduction component A1S, and A2 can be similarly resolved into a rotation component referred to as A2R and an expansion/reduction component A2S. Therefore, the rotational component BR of B is obtained by temporally interpolating each element of the matrix of A1R and A2R, and the scaling factor BS of B is obtained by temporally interpolating each element of the matrix of A1S and A2S. By integrating BR and BS obtained in this way, the positional deviation amount B can be calculated.

Figure 9:
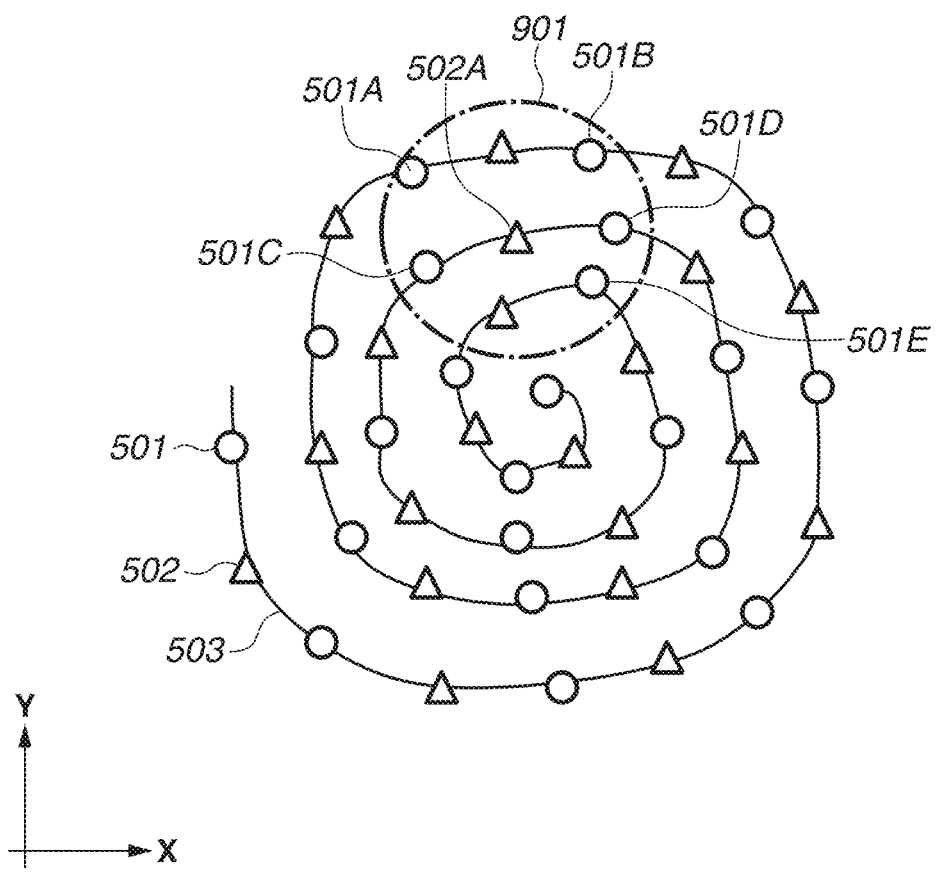
FIG. 9 is another schematic diagram illustrating a measurement position of the photoacoustic apparatus according to the first exemplary embodiment.

Alternatively, interpolation may be performed spatially to calculate the positional deviation amount of spatially nearby pulses. FIG. 9 is a schematic diagram illustrating a position (measurement position) of the probe 180 when applying a pulse of a plurality of wavelengths while performing spatial scanning as in FIG. 5. A case where positional deviation information corresponding to a measurement position 502A corresponding to the timing of irradiation with light of the wavelength λ2 is obtained by spatially interpolating the positional deviation information corresponding to the wavelength λ1 will be described. The arithmetic unit 151 determines a measurement position of the wavelength λ1 corresponding to a measurement position near the measurement position 502A. For example, the measurement position of the wavelength λ1 included in the predetermined distance from the measurement position 502A of the wavelength λ2 is determined. A chain line 901 indicates a range of a predetermined distance from the measurement position 502A. The measurement positions 501A, 501B, 501C, 501D, and 501E of the wavelength λ1 indicate measurement positions of the wavelength λ1 included at a predetermined distance from the measurement position 502A of the wavelength λ2. Therefore, by spatially interpolating positional deviation information corresponding to the measurement positions 501A, 501B, 501C, 501D, and 501E of the wavelength λ1, the arithmetic unit 151 obtains positional deviation information corresponding to the measurement position 502A of the wavelength λ2. As a method for spatially interpolating, fitting of the function may be performed on positional deviation information already calculated and positional deviation information at a desired position may be obtained from the function. As a method for spatially interpolating, weighting according to the distance may be added, and positional deviation information at a desired position may be calculated. In the following description, a method for calculating desired positional deviation information of pulse volume data will be described below, by weighting the positional deviation information of the pulse volume data within a predetermined distance from the measurement position for which the positional deviation information is desired according to the distance.

Here, the position irradiated with the pulse is taken as the center coordinates of the pulse volume data. Furthermore, N is the number of pulses of positional deviation information of pulse volume data of wavelength λ1 included in the range of radius Rmm from a center coordinate $POS_{result}$ of the pulse volume data $P_{result}$ of the wavelength λ2 for which the positional deviation information is desired. Further, when the positional deviation amount (translational amount) as the positional deviation information is $Mi$ (1≤i≤N) \hfill Expression 11 and a center coordinate is $POSi$ (1≤i≤N) \hfill Expression 12 the positional deviation amount $M_{result}$ of $P_{result}$ can be calculated by the following Expressions.

$$M_{result} = \frac{\sum_{i=1}^{N} \omega_i M_i}{\sum_{i=1}^{N} \omega_i} \quad \quad \text{Expression 13}$$

For example, in FIG. 9, the reference numeral 502A represents a measurement position corresponding to the center coordinate $POS_{result}$ of the pulse volume data $P_{result}$ of wavelength λ2 for which positional deviation information is desired. In addition, reference numeral 901 represents a range of a radius Rmm from the measurement position 502A. Reference numerals 501 A to 501E indicate measurement positions corresponding to the center coordinates of the pulse volume data included in the range 901.

In this case, $ω_i$ is the weight calculated from the distance, and the spatial distance between $POS_i$ and $POS_{result}$ can be calculated using $$\overline{POS_iPOS_{result}} \quad \text{Expression 14}$$

by the following equation.

$$ω_i = \frac{1}{\overline{POS_iPOS_{result}}}, \quad \text{Expression 15}$$

provided that $\overline{POS_iPOS_{result}} \leq R$

When spatially interpolating, spatial interpolation may be performed using any pulse volume, without being limited to the above method. For example, when a nearest pulse is used, or when a spiral scanning is performed a plurality of times, two neighboring pulses or all the pulses may be used in each circulation.

In this way, it is possible to calculate positional deviation information of a pulse with other wavelength from positional deviation information corresponding to the measurement position spatially close to the measurement position of the specific wavelength.

In the case of applying light with three or more wavelengths, a method for obtaining positional deviation information according to the present exemplary embodiment may be applied. In this case, the positional deviation information obtained at a specific wavelength may be used to obtain other positional deviation information of a plurality of wavelengths. In addition, positional deviation information of other wavelengths may be obtained using positional deviation information obtained at a plurality of wavelengths including a wavelength suitable for obtaining positional deviation information. In other words, the positional deviation information of other wavelengths may be obtained using positional deviation information obtained with at least one wavelength.

Furthermore, when positional deviation information is obtained, taking deformation using a deformed alignment technique such as FFD into consideration, the positional deviation information may be a deformation field. A deformation field is a field of deformation from a deformation image to a reference image.

Figure 10:
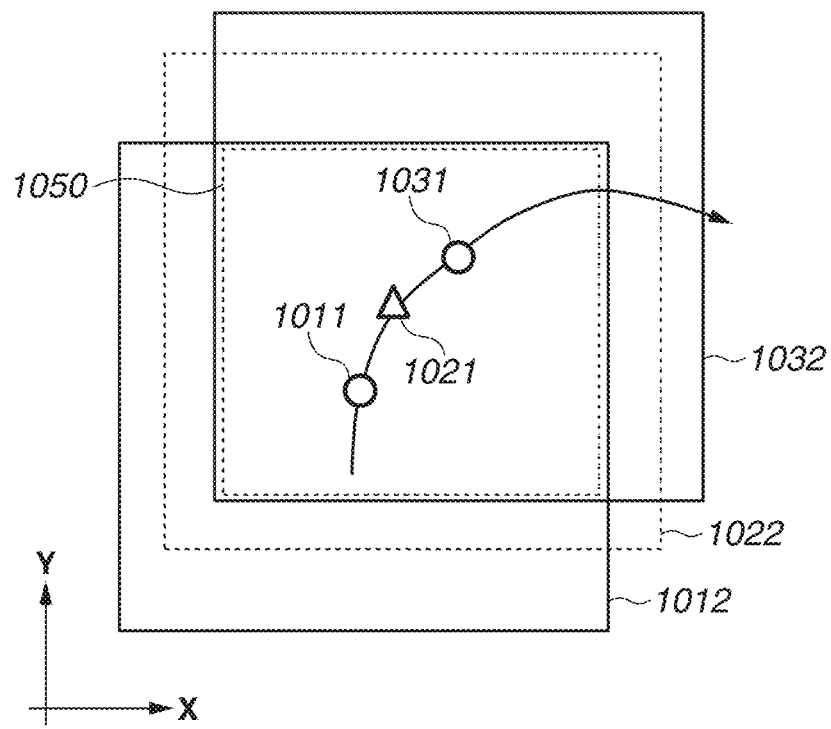
FIG. 10 is still another schematic diagram illustrating a measurement position of the photoacoustic apparatus according to the first exemplary embodiment.

An example of the case where the positional deviation information is a deformation field will be described with reference to FIG. 10. Here, for the sake of convenience, the three-dimensional image data region will be described as a two-dimensional plane of XY. Reference numerals 1011 and 1031 denote pulse irradiation positions at the wavelength λ1, reference numerals 1012 and 1032 denote image data regions of the pulse, and a region indicated by a dotted line of reference numeral 1050 is an overlapping region of images of reference numerals 1012 and 1032. Reference numeral 1021 denotes a pulse irradiation position at the wavelength λ2, and reference numeral 1022 denotes an image data region corresponding to the pulse 1021. Here, it is assumed that reference numerals 1011, 1031 and 1021 are irradiated at times t1, t2 and (t1+t2)/2, respectively.

Herein, it is considered that deforming alignment of the image 1012 is performed with reference to the image 1032 in the overlapping region 1050 of reference numeral 1012 and reference numeral 1032. Then, it is possible to calculate a three-dimensional deformation field of the size of the overlapping region 1050.

The deformation field of the region 1050 in the image data region 1022 can be calculated from the deformation field of the image 1012 based on the image 1032. As a calculation method, assuming that deformation of the image 1012 with reference to the image 1032 has occurred linearly with passage of time at time t2−t1, the deformation field of the region 1050 is obtained by interpolating the deformation field with time. More specifically, (t2−(t1+t2)/2)/(t2−t1) may be integrated.

In this example, from the deformation field between two images, the deformation field from one image of the image at the intermediate time has been calculated. Accordingly, for each image data of pulses alternately applied with a plurality of wavelengths, it is possible to calculate the deformation field of images of other wavelengths captured between the image capturing times of the two images having overlapping regions in one wavelength. By applying this to all imaging pulses with a plurality of wavelengths, it is possible to calculate the deformation field to each pulse based on the image data of any pulse at all wavelengths.

As another example, when a plurality of deformation fields is required among image data of a plurality of pulses, by temporally interpolating from the plurality of deformation fields, it is possible to calculate the deformation field of the pulse applied at the time near the interpolation time. In order to calculate the deformation field, focusing on the amount of displacement in a deformation field of a certain voxel in the image data, it is tracked how each voxel in the deformation field is displaced in a plurality of deformation fields between image data captured at discrete times. From the amount of displacement over time, the deformation field at a certain time may be calculated.

It is preferable to select the wavelength λ1 as a reference by which the positional deviation information can be obtained with high obtaining accuracy. Therefore, for example, the arithmetic unit 151 calculates an evaluation index indicating image quality such as pulse volume data and synthesized volume data generated using each of a plurality of wavelengths, resolution such as MIP image, or signal-to-noise (SN) ratio. Then, the arithmetic unit 151 may obtain the positional deviation information with the wavelength at which the evaluation index indicating the calculated image quality is good, as the wavelength λ1.

In the case where the positional deviation information is obtained by temporally interpolating, the arithmetic unit 151 may determine the wavelength of the light which is applied many times within a predetermined period, and may set the wavelength as the wavelength λ1. For example, the arithmetic unit 151 may set the wavelength of the light which is applied most frequently within a predetermined period, as the wavelength λ1 in the predetermined period. In addition, the arithmetic unit 151 may set the wavelength of the light which is applied more than the predetermined number of times in the predetermined period, as the wavelength λ1 within the predetermined period. Further, a plurality of wavelengths may be set as the wavelength λ1.

In addition, when it can be considered that the irradiation timing between wavelengths is substantially the same, the positional deviation information corresponding to the irradiation timing with the light of the wavelength λ1 may be obtained as the positional deviation information corresponding to the irradiation timing with the light of the wavelength λ2. For example, the positional deviation amount obtained in step S300 can be used as it is for pulses of other wavelengths.

For example, when an irradiation interval of pulsed light between a plurality of wavelengths is so short that the irradiation interval can be neglected with respect to the movement of the object, the irradiation timings between the wavelengths can be regarded as substantially the same. For example, in the case of the body movement due to breathing of a living body, an irradiation interval between wavelengths can be substantially the same. It is assumed that the living body linearly displaces due to respiration with a cycle of 3 seconds and the maximum displacement amount of 3 mm. When the tolerance of the resolution of the acoustic image is set to 0.25 mm, if the irradiation interval is within 125 ms, the irradiation timings between the wavelengths may be considered to be substantially the same. At this time, it is assumed that the displacement amount of the living body is directly reflected in the error of the resolution of the photoacoustic image. Furthermore, if the tolerance of the resolution of the photoacoustic image is set to 0.1 mm, the irradiation timings between wavelengths may be regarded as substantially the same as long as the irradiation interval is within 50 ms.

Furthermore, the arithmetic unit 151 may interpolate the positional deviation information obtained in step S300 or step S400 temporally or spatially, to use the interpolated positional deviation information as positional deviation information of images obtained by other modalities.

(Step S500: Step of Performing Positional Deviation Correction Based on Positional Deviation Information Corresponding to Irradiation Timing with Light of Wavelength λ1 and Wavelength λ2)

The arithmetic unit 151 performs positional deviation correction based on the positional deviation information corresponding to the wavelength λ1 obtained in step S300 and the positional deviation information corresponding to the wavelength λ2 obtained in step S400.

For example, based on the positional deviation information corresponding to the wavelength λ1 obtained in step S300, the arithmetic unit 151 may perform positional deviation correction processing on the position information of the pulse volume data of the wavelength λ1 obtained in step S200. Furthermore, the arithmetic unit 151 may generate pulse volume data corresponding to the wavelength λ2 based on the signal group obtained in step S100. Then, the arithmetic unit 151 may perform processing of correcting the position of the pulse volume data of the wavelength λ2 by the positional deviation amount, based on the positional deviation information corresponding to the wavelength λ2 obtained in step S400. Furthermore, the arithmetic unit 151 may synthesize the pulse volume data of wavelength λ1 and the pulse volume data of wavelength λ2 in which positional deviation has been corrected, to perform alignment, thereby generating synthesized volume data.

Hereinafter, an example of correcting the positional deviation of the pulse volume having the wavelength λ1 will be described. FIGS. 11A to 11E illustrate an example of positional deviation correction processing (parallel processing) in this step.

Figure 11A:
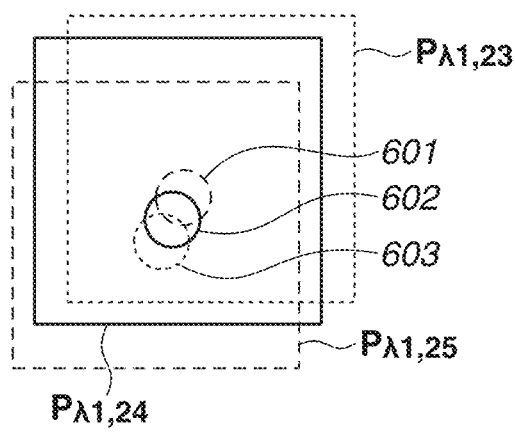
FIGS. 11A to 11E are schematic diagrams for explaining positional deviation correction according to the first exemplary embodiment.

FIG. 11A illustrates a part ($P_{\lambda1,23}$ to $P_{\lambda1,25}$) of the pulse volume data before parallel processing in the present exemplary embodiment. A dashed line represents the outer circumference of $P_{\lambda1,25}$ and a feature 601 in $P_{\lambda1,25}$. A solid line represents the outer circumference of $P_{\lambda1,24}$ and inner feature 602 in $P_{\lambda1,24}$. A dotted line represents the outer circumference $P_{\lambda1,23}$ and inner feature 603 in $P_{\lambda1,23}$. The features 601, 602, and 603 all represent the same feature. In FIG. 11A, the features in each pulse volume data are located at different positions.

Figure 11B:
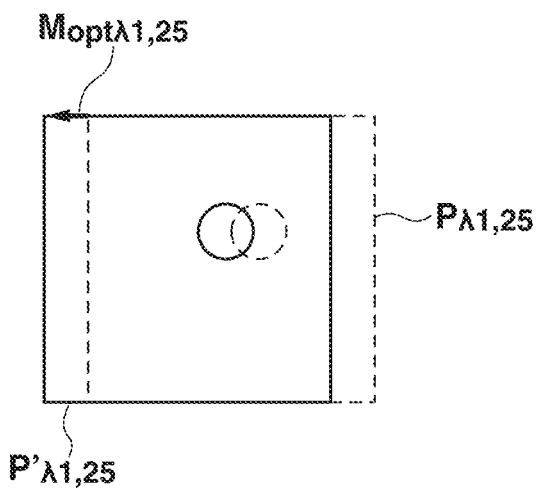
Figure 11C:
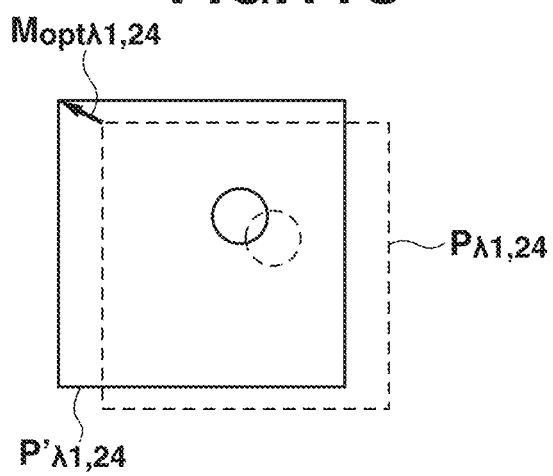

FIG. 11B illustrates pulse volume data $P'_{\lambda1,25}$ after translating pulse volume data $P_{\lambda1,25}$ present before translation, by a positional deviation amount $Mopt_{\lambda1},25$ estimated by the above method. FIG. 11C illustrates pulse volume data $P'_{\lambda1,24}$ after translating pulse volume data $P_{\lambda1,24}$ present before translation, by a positional deviation amount $Mopt_{\lambda1},24$ estimated by the above method.

Figure 11D:
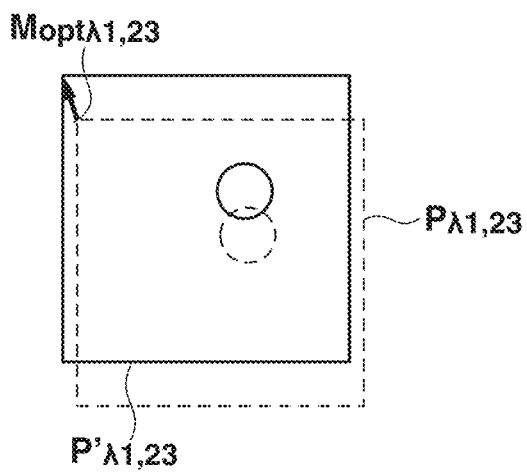

FIG. 11D illustrates pulse volume data $P'_{\lambda1,23}$ after translating pulse volume data $P_{\lambda1,23}$ present before translation, by a positional deviation $Mopt_{\lambda1,}23$ estimated by the above method.

Figure 11E:
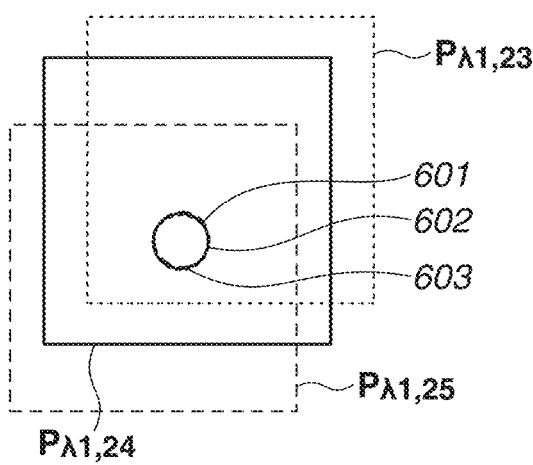

FIG. 11E illustrates the superposed pulse volume data $P'_{\lambda1,23}$, $P_{\lambda1,24}$, and $P'_{\lambda1,25}$ after translation. In FIG. 11E, the features 601, 602, and 603 in each pulse volume data overlap at almost the same position. As illustrated in FIG. 11E, the arithmetic unit 151 can obtain the aligned volume data by synthesizing each pulse volume data subjected to translation processing. The aligned volume data corresponds to the synthesized volume data. "Alignment" refers to performing both positional deviation correction processing and synthesized processing.

Further, for example, in the reconstruction processing, based on the positional deviation information corresponding to the wavelength λ1 obtained in step S300, the arithmetic unit 151 may correct the position information of the receiving unit 120 corresponding to the irradiation timing of the wavelength λ1 only by the positional deviation amount. Further, in the reconstruction processing, based on the positional deviation information corresponding to the wavelength λ2 obtained in step S400, the arithmetic unit 151 may correct the position information of the receiving unit 120 corresponding to the irradiation timing of the wavelength λ2 only by the positional deviation amount. The arithmetic unit 151 may perform reconstruction processing based on the signal group obtained in step S100 and the position information of the receiving unit 120 whose positional deviation corresponding to the irradiation timing with the light of the wavelength λ1 and the wavelength λ2 has been corrected, thereby generating synthesized volume data.

Here, an example of a method for performing positional deviation correction of position information of the receiving unit 120 will be described. First, the arithmetic unit 151 obtains the position information of the receiving unit 120 when the positional deviation is not taken into consideration. For example, the arithmetic unit 151 may obtain the position information when the positional deviation is not taken into consideration, by reading the position information of the receiving unit 120 at the time of light irradiation which is stored in the storage unit 152 in advance. In addition, the arithmetic unit 151 may obtain the position information of the receiving unit 120 when the positional deviation is not taken into consideration, by receiving the position information of the receiving unit 120 from the position sensor provided in the driving unit 130 in response to light irradiation as a trigger.

Subsequently, the arithmetic unit 151 corrects the position information of the receiving unit 120 when the positional deviation at the time of light irradiation is not taken into account, by the positional deviation amount which is indicated by the positional deviation information obtained in step S300 or step S400 (for example, translation processing).

As a result, the arithmetic unit 151 can obtain the position information of the receiving unit 120 in which positional deviation has been corrected at the time of light irradiation. That is, the arithmetic unit 151 can obtain the position information of the receiving unit 120 in which positional deviation has been corrected, based on the positional deviation information obtained in step S300 or step S400.

The arithmetic unit 151 obtains the synthesized image data based on the signal group obtained in step S100 and the position information of the receiving unit 120 in which positional deviation has been corrected. In this step, the arithmetic unit 151 reconstructs a region which is smaller than the entire imaging region, from the signal corresponding to one light irradiation. The reconstruction may be repeated for the plurality of light irradiation, to generate one volume data. In this case, in the step, the arithmetic unit 151 obtains a plurality of pulse volume data corresponding to the plurality of light irradiations, and synthesizes the image data group. Furthermore, the arithmetic unit 151 may generate one volume data by reconstructing the entire imaging region from the signal group corresponding to the plurality of light irradiations.

Processing similar to the above can be performed also when synthesizing data corresponding to a plurality of wavelengths. Besides the addition processing and the averaging processing of data corresponding to a plurality of wavelengths, processing of obtaining function information such as oxygen saturation by comparing and calculating data corresponding to a plurality of wavelengths is included in the exemplary embodiments. Hereinafter, a method for obtaining oxygen saturation as function information using data corresponding to a plurality of wavelengths will be described.

Assuming that light absorption other than hemoglobin is negligibly low at wavelength λ1 and wavelength λ2, the absorption coefficients of the wavelengths λ1 and λ2 are expressed by Expressions 16 and 17 using the molar absorption coefficient of oxyhemoglobin and the molar absorption coefficient of deoxyhemoglobin, respectively.

$$\mu_a(\lambda_1) = \varepsilon_{ox}(\lambda_1)C_{ox} + \varepsilon_{de}(\lambda_1)C_{de} \quad \text{Expression 16}$$

$$\mu_a(\lambda_2) = \varepsilon_{ox}(\lambda_2)C_{ox} + \varepsilon_{de}(\lambda_2)C_{de} \quad \text{Expression 17}$$

Here, $\mu_a(\lambda_1)$ is the absorption coefficient of light at wavelength λ1 at position (i,j,k), $\mu_a(\lambda_2)$ is the absorption coefficient of light at wavelength λ2 at the position (i,j,k), and unit can be indicated by [mm$^{-1}$]. $C_{ox}$ is the amount of oxyhemoglobin [mol], and $C_{de}$ is the amount of deoxyhemoglobin. Both values indicate values at the position (i,j,k).

$\varepsilon_{ox}(\lambda_1)$ and $\varepsilon_{de}(\lambda_1)$ respectively represent the molar absorption coefficient [mm$^{-1}$ mol$^{-1}$] of oxyhemoglobin and deoxyhemoglobin at the wavelength λ1. $\varepsilon_{ox}(\lambda_2)$ and $\varepsilon_{de}(\lambda_2)$ respectively indicate the molar absorption coefficient [mm$^{-1}$mol$^{-1}$] of oxyhemoglobin and deoxyhemoglobin at wavelength λ2. $\varepsilon_{ox}(\lambda_1)$, $\lambda_{de}(\lambda_1)$, $\varepsilon_{ox}(\lambda_2)$, and $\varepsilon_{de}(\lambda_2)$ can be obtained in advance from measurement or literature values.

Therefore, $C_{ox}$ and $C_{de}$ are obtained by solving the simultaneous equations of Expressions 16 and 17, respectively, using the molar extinction coefficient and $\mu_a(\lambda_1)$ and $\mu_a(\lambda_2)$. If the number of wavelengths to be used is large, the least squares method may be used. Furthermore, the oxygen saturation SO$_2$ is defined by the ratio of oxyhemoglobin in total hemoglobin as illustrated in Expression 18. Therefore, the oxygen saturation SO$_2$ can be expressed by Expression 19 based on Expressions 16, 17, and 18.

Therefore, the arithmetic unit 151 can obtain the oxygen saturation SO$_2$ at the position (i,j,k) based on the molar extinction coefficient and $\mu_a(\lambda_1)$ and $\mu_a(\lambda_2)$ according to Expression 19.

$$SO_2 = \frac{C_{ox}}{C_{ox} + C_{de}} \quad \text{Expression 18}$$

$$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad \text{Expression 19}$$

By performing such processing on a plurality of positions, oxygen saturation at a plurality of positions can be obtained, and an oxygen saturation distribution can be obtained. The oxygen saturation distribution is obtained by comparative calculation of the absorption coefficient distribution (for example, processing for calculating ratio). If the values of absorption coefficients at multiple wavelengths are relatively correct, the oxygen saturation distribution can be properly determined. Therefore, it is not necessary to accurately obtain the absorption coefficient distribution as an absolute value.

In the present embodiment, the initial sound pressure image in which the influence of positional deviation is reduced has been calculated, and an absorption coefficient image and an oxygen saturation level image have been calculated therefrom. However, embodiments are not limited to this method. Pulse volume data of a plurality of wavelengths may be obtained as an absorption coefficient distribution image, and the positional deviation amount may be calculated from the absorption coefficient distribution image at one of the wavelengths. Furthermore, by applying the positional deviation amount calculated in this way to other wavelengths, absorption coefficient images in which the influence of positional deviation is reduced may be calculated, and oxygen saturation level images may be calculated from these absorption coefficient images.

With this configuration, by obtaining an absorption coefficient image in which the influence of misalignment is reduced among images of a plurality of wavelengths, and synthesizing an absorption coefficient image in which the influence of misalignment is reduced, it becomes possible to calculate the oxygen saturation level image.

By this method, it is possible to obtain image data (position-adjusted volume data) in which the influence of variation in the relative positional relationship between the object and the photoacoustic wave receiving unit during light irradiation is suppressed.

The above processing can be applied even when the receiving unit 120 does not move between light irradiations. In other words, even when the photoacoustic apparatus does not have the driving unit 130, the above-described processing can be applied. Furthermore, in this case, it is possible to obtain image data in which the influence of the change in the relative positional relationship between the object and the photoacoustic wave receiving unit between the plurality of light irradiations is suppressed.

In addition, when imaging by the photoacoustic apparatus is performed together with a modality (for example, an ultrasonic diagnostic apparatus or the like) which is different from the photoacoustic apparatus, the positional deviation information obtained by the photoacoustic apparatus may be used to obtain positional deviation information about another modality. For example, the arithmetic unit 151 may obtain positional deviation information of image data obtained with another modality by temporally or spatially interpolating the positional deviation information obtained in step S300, step S400, or step S500. Furthermore, when the photoacoustic apparatus and the other modality generate image data at substantially the same position, at substantially the same time, positional deviation information obtained by the photoacoustic apparatus may be used as positional deviation information about another modality.

For example, when an ultrasonic diagnostic apparatus is assumed as another modality, an inspection system including the photoacoustic apparatus includes an ultrasound transceiver unit. The transceiver unit transmits an ultrasonic wave to the object and outputs an ultrasonic signal by receiving an echo wave of the transmitted ultrasonic wave. The transceiver unit includes a transducer that outputs an electrical signal by receiving an acoustic wave. The transceiver unit may include a plurality of transducers. In addition, the transceiver unit may separately prepare a transducer for transmitting an ultrasonic wave and a transducer for receiving an acoustic wave. Furthermore, the transducer for transmitting an ultrasonic wave and the transducer for receiving an acoustic wave may include the same transducer. Furthermore, a transducer for transmitting and receiving an ultrasonic wave and a transducer for receiving a photoacoustic wave may be separately prepared. Furthermore, the transducer for transmitting and receiving an ultrasonic wave and the transducer for receiving a photoacoustic wave may be the same transducer.

Hereinafter, the configuration and processing of the photoacoustic apparatus of the second exemplary embodiment will be described. In the second exemplary embodiment, the same apparatus as the photoacoustic apparatus of the first exemplary embodiment is used. In the second exemplary embodiment, the same reference numerals are given to the same components as those of the photoacoustic apparatus of the first exemplary embodiment, and a detailed description thereof will be omitted.

As described above, in the case of using light with a plurality of wavelengths, there is a possibility that a wavelength showing low accuracy in estimating positional deviation between a plurality of image data is included. In this case, if only the image data group obtained by the object wavelength is used, it is difficult to accurately obtain positional deviation information corresponding to the irradiation timing with light of the wavelength. Specifically, when light with a plurality of wavelengths is used, variation occurs in the estimation accuracy of positional deviation between wavelengths.

Therefore, the photoacoustic apparatus according to one exemplary embodiment of the present invention obtains positional deviation information between a plurality of image data for each of a plurality of different wavelengths. Then, by combining the positional deviation information obtained for each of the plurality of wavelengths, the positional deviation information obtained earlier is updated. As a result, even when a wavelength that shows the low estimation accuracy is included, the obtained positional deviation information is updated using the positional deviation information obtained with a wavelength showing relatively high accuracy in estimating positional deviation, so that it is possible to accurately obtain positional deviation information.

More specifically, in the photoacoustic apparatus according to one exemplary embodiment of the present invention, the object is irradiated with light of the first wavelength and light of the second wavelength which are different from each other, a plurality of times. Then, a first image data group corresponding to the first wavelength is generated, and positional deviation information between the first image data groups is obtained. The obtained positional deviation information corresponds to a variation amount (positional deviation amount) in the relative position between the object and the probe corresponding to the irradiation timing with the light of the first wavelength. In addition, a second image data group corresponding to the second wavelength is generated, and positional deviation information between the second image data group is obtained. Then, based on the first positional deviation information and the second positional deviation information, the positional deviation information corresponding to the irradiation timing with the light of the first and second wavelengths is updated. Thus, since the positional deviation information obtained from the wavelength showing high accuracy in estimating the positional deviation is also used when obtaining the positional deviation information about the wavelength showing low accuracy in estimating the positional deviation, variation of estimation accuracy of positional deviation between wavelengths becomes small.

Furthermore, by changing the weight for the position deviation information when combining the positional deviation information of the respective wavelengths, the estimation result of the wavelength showing high estimation accuracy can be prioritized.

The method described in the first exemplary embodiment can be applied to obtaining a signal group and obtaining positional deviation information corresponding to light irradiation timing of each wavelength in the present case.

Figure 12:
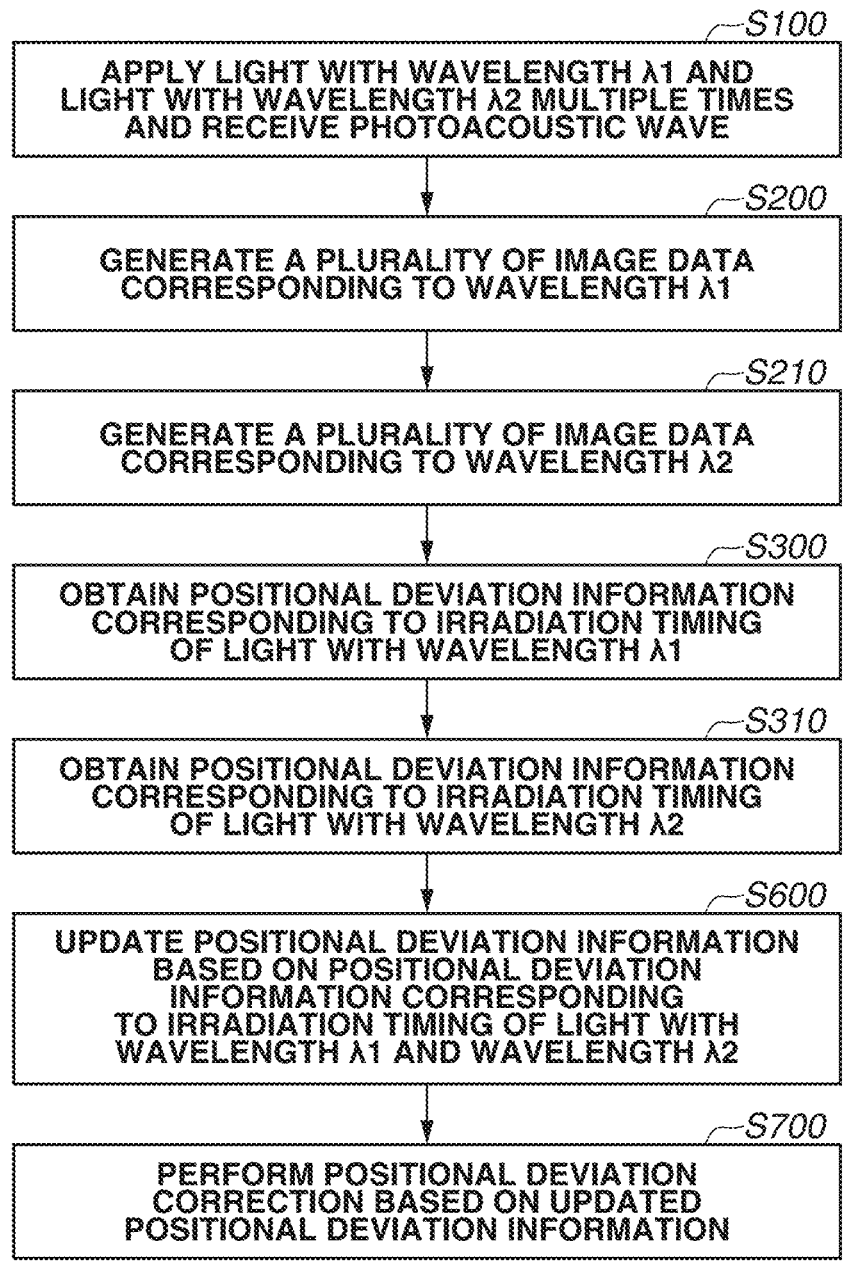
FIG. 12 is a flow chart illustrating an operation of the photoacoustic apparatus according to a second exemplary embodiment.

The operation of the photoacoustic apparatus including information processing according to the present exemplary embodiment will be described below along a flow chart illustrated in FIG. 12. The same steps as in the step illustrated in FIG. 4 are denoted by the same reference numerals, and the detailed explanation is omitted.

(Step S210: Step of Generating Image Data Group Corresponding to Wavelength $\lambda 2$)

The arithmetic unit 151 obtains an image data group corresponding to the light irradiation of the second wavelength based on the signal group obtained in step S100 as in step S200. In the present exemplary embodiment, an example of obtaining a plurality of pieces of image data corresponding to the light irradiation of the second wavelength will be described. However, the present invention can also be applied to a case where one image data is obtained.

(Step S310: Step of Obtaining Positional Deviation Information Corresponding to Irradiation Timing with Light of Wavelength $\lambda 2$)

Based on the image data group corresponding to the wavelength $\lambda 2$ obtained in step S210, as in step S300, the arithmetic unit 151 obtains positional deviation information corresponding to the irradiation timing with the light of the wavelength $\lambda 2$.

(Step S600: Step of Updating Positional Deviation Information Based on Positional Deviation Information at Irradiation Timing with Light of Wavelength $\lambda 1$ and Wavelength $\lambda 2$)

The arithmetic unit 151 updates the positional deviation information based on the positional deviation information corresponding to the irradiation timing with the light of the wavelength $\lambda 1$ obtained in step S300 and the positional deviation information corresponding to the irradiation timing with the light of the wavelength $\lambda 2$.

As an example, a case is considered where the arithmetic unit 151 calculates a translation amount Mopt_st$_{\lambda 1}$ as positional deviation information corresponding to the irradiation timing with the light of the wavelength λ1 in step S300 and calculates a translation amount Mopt_st$_{\lambda 2}$ as the positional deviation information corresponding to the irradiation timing with the light of the wavelength λ2 in step S310. At this time, in this step, the arithmetic unit 151 may update the positional deviation information Mopt_st$_{\lambda 1}$ and Mopt_st$_{\lambda 2}$ of each wavelength by averaging the positional deviation information as illustrated in Expression 20.

$$Mopt\_st_{\lambda 1}=(Mopt_{\lambda 1}+Mopt_{\lambda 2})/2 \quad Mopt\_st_{\lambda 2}=(Mopt_{\lambda 1}+Mopt_{\lambda 2})/2 \quad \text{Expression 20}$$

In addition, the arithmetic unit 151 may update the positional deviation information of each wavelength by temporally or spatially performing interpolation using the positional deviation information of each wavelength as described in the first exemplary embodiment.

Furthermore, the arithmetic unit 151 may update the positional deviation information of each wavelength by weighting the positional deviation information of each wavelength. The arithmetic unit 151 may update the positional deviation information of each wavelength by weighting the positional deviation information of each wavelength using a predetermined weight. Alternatively, the arithmetic unit 151 may weigh the positional deviation information of each wavelength using the weight determined by the instruction made by the user using the input unit 170.

(Step S700: Step of Performing Positional Deviation Correction Based on Updated Positional Deviation Information)

Based on the positional deviation information corresponding to the irradiation timing with the light of the wavelength λ1 and the wavelength λ2 updated in step S600, the arithmetic unit 151 performs positional deviation correction in the same method as described in step S500.

In the present exemplary embodiment, since the combined positional deviation information is employed using not only positional deviation information obtained by a wavelength showing low accuracy in estimating positional deviation but also positional deviation information obtained from a wavelength showing high accuracy in estimating positional deviation, variation of estimation accuracy of positional deviation between wavelengths becomes small.

Figure 13:
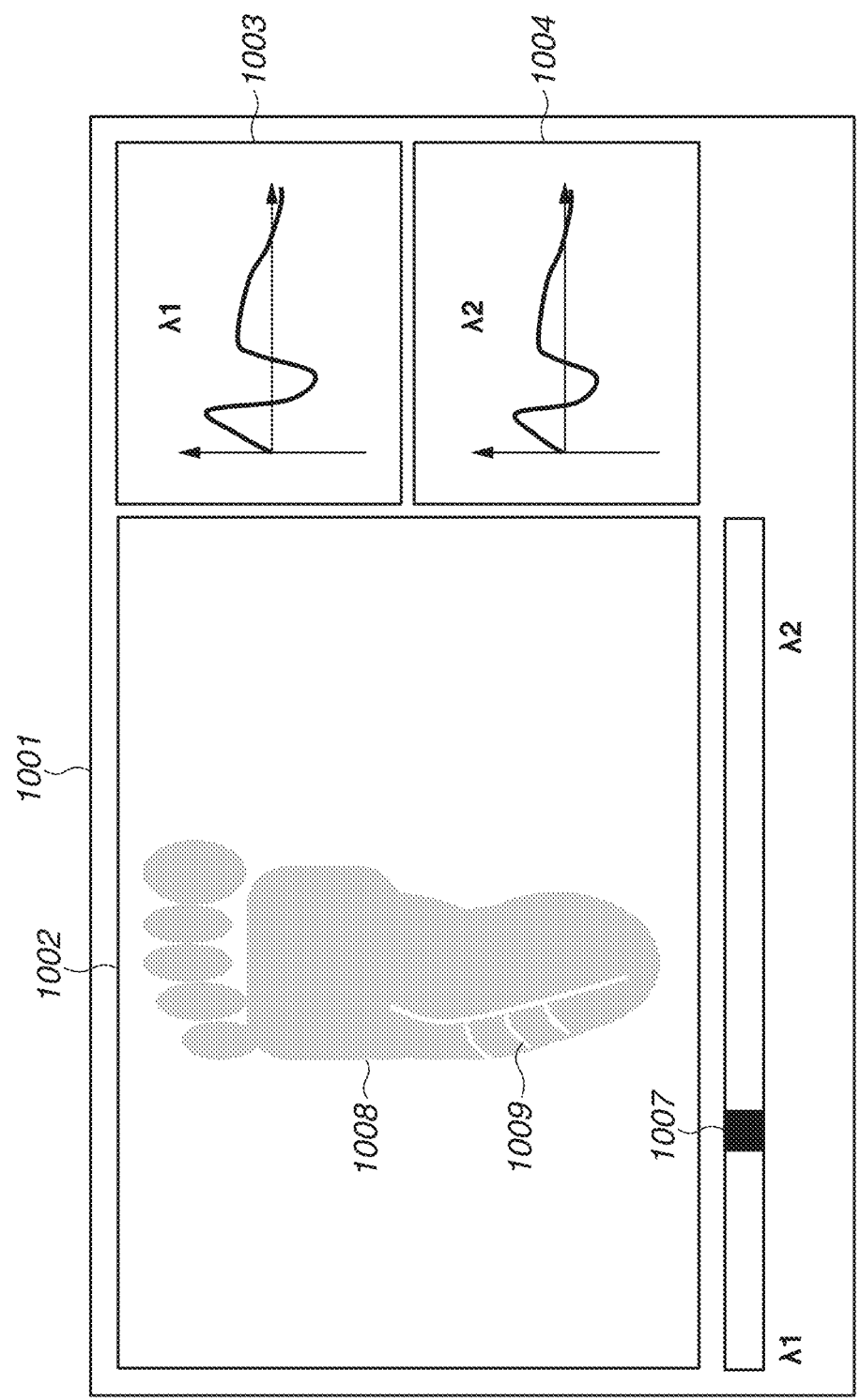
FIG. 13 is a schematic diagram illustrating a graphical user interface (GUI) according to the second exemplary embodiment.

FIG. 13 illustrates a schematic diagram of a GUI having a slider for determining the weight for positional deviation information of each wavelength. For example, it is possible to determine the weight by using the GUI as illustrated in FIG. 13 displayed on the display unit 160.

On a GUI 1001, a display region 1002 of the photoacoustic image, a graph 1003 of the positional deviation amount of the wavelength λ1, and a graph 1004 of the positional deviation amount of the wavelength λ2 are displayed. In the graphs 1003 and 1004, the vertical axis represents the amount of positional deviation and the horizontal axis represents the pulse index. That is, the graphs 1003 and 1004 plot the positional deviation amount with respect to the pulse volume data at the wavelength λ1 and the wavelength λ2. A slider bar 1007 is an item for determining the weight of position deviation amounts of a plurality of wavelengths. When the slider bar 1007 is manipulated to the left, the positional deviation amount of the wavelength λ1 is dominantly added. When the slider bar 1007 is operated to the right, the positional deviation amount of the wavelength λ2 is dominantly added. That is, when the slider bar 1007 is manipulated to the left, the weight of the wavelength λ1 is increased. When the slider bar 1007 is manipulated to the right, the weight of the wavelength λ2 is increased, and the weighted final positional deviation amount is determined.

Then, a photoacoustic image obtained using the weighted final positional deviation amount is displayed in the display region 1002. Further, when the user operates the slider bar 1007, the final positional deviation amount is recalculated and updated. Then, using the updated positional deviation amount, the photoacoustic image is obtained again, and the photoacoustic image displayed in the display region 1002 is updated. In FIG. 13, the photoacoustic image 1008 of the foot is displayed in the display region 1002, and a photoacoustic image 1008 includes a blood vessel image 1009.

By using such a GUI, weights for positional deviation amounts at a plurality of wavelengths are changed and determined with a slider bar 1007, so that it is possible to determine the final positional deviation amount while confirming the change of the image quality (resolution, or the like) of the photoacoustic image displayed in the display region.

Hereinafter, the configuration and processing of the photoacoustic apparatus of the third exemplary embodiment will be described. In the third exemplary embodiment, the same apparatus as the photoacoustic apparatus of the first or second exemplary embodiment is used. In the third exemplary embodiment, the same reference numerals are given to the same components as those of the photoacoustic apparatus of the first or second exemplary embodiment, and a detailed description thereof will be omitted.

As described above, in the case of using light beams with a plurality of different wavelengths, the image characteristics such as the image intensity may be differentiated between wavelengths in some cases. In that case, since the image intensity varies between wavelengths, the accuracy in estimating the positional deviation may decrease.

Therefore, based on a photoacoustic wave generated by irradiation with light of each of a plurality of mutually different wavelengths, the photoacoustic apparatus according to one exemplary embodiment of the present invention generates image data using light of each wavelength. Then, after performing processing so as to reduce the difference in image characteristics between wavelengths, positional deviation information is obtained using image data group with a plurality of wavelengths. As a result, it is possible to suppress degradation of estimation accuracy of positional deviation caused by difference in image characteristics between wavelengths.

More specifically, in the photoacoustic apparatus according to one exemplary embodiment of the present invention, the object is irradiated with respective light of the first wavelength and light of the second wavelength which are different from each other a plurality of times. Then, a first image data group corresponding to the first wavelength is generated. In addition, a second image data group corresponding to the second wavelength is generated. Then, image processing is performed on at least one of the first image data group and the second image data group so that the difference in image characteristics between the first image data group and the second image data group is reduced. Then, by using the first image data group and the second image data group after the processing of reducing the difference in image characteristics is performed, positional deviation information corresponding to the irradiation timing with light of the first and second wavelengths is obtained.

In the above description, an example in which the difference in image characteristics between wavelengths is reduced by image processing on image data has been described. However, the difference in the image characteristics between the wavelengths may be reduced by the signal processing on the signal before being converted into the image data.

Figure 14:
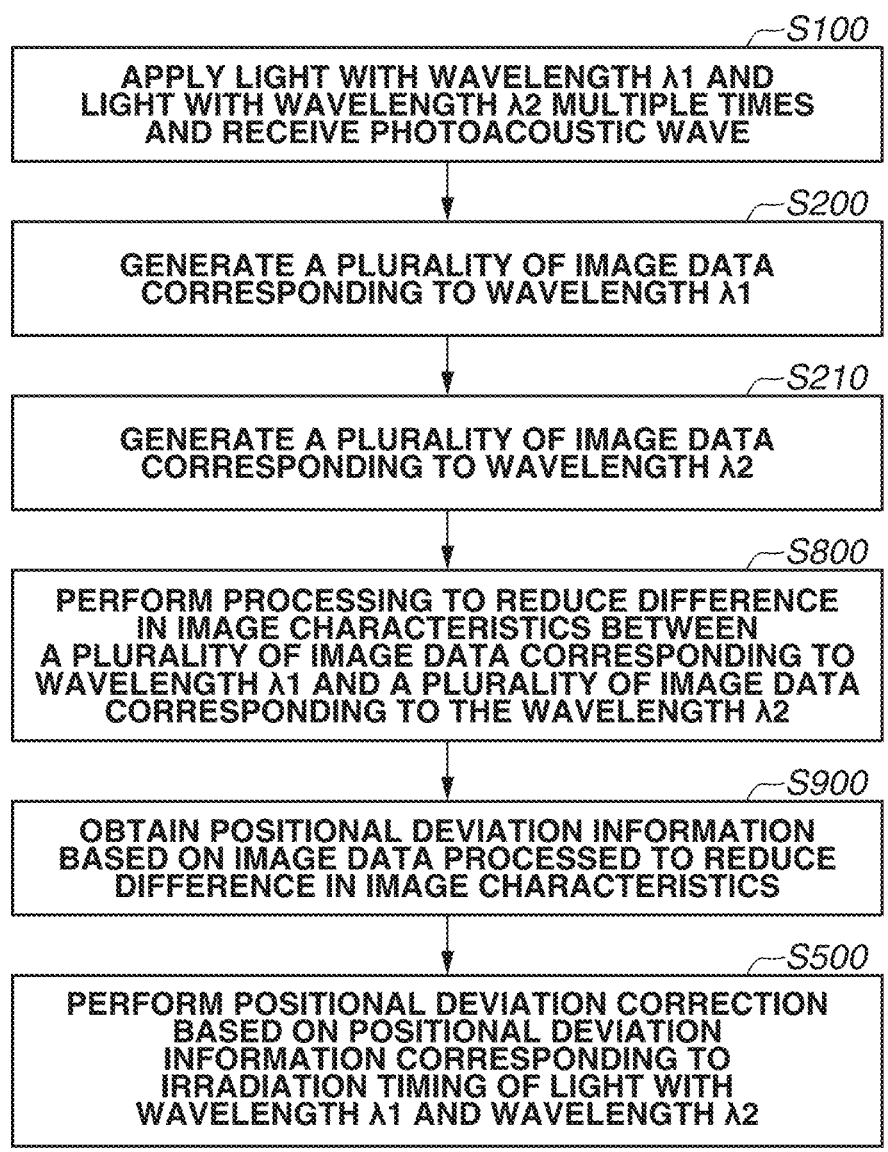
FIG. 14 is a flow chart illustrating an operation of the photoacoustic apparatus according to a third exemplary embodiment.

The operation of the photoacoustic apparatus including information processing according to the present exemplary embodiment will be described below along a flow chart illustrated in FIG. 14. The same steps as in the step illustrated in FIG. 4 are denoted by the same reference numerals, and the detailed explanation is omitted.

(Step S800: Step of Performing Processing for Reducing Difference in Image Characteristics Between Image Data Group Corresponding to Wavelength λ1 and Image Data Group Corresponding to Wavelength λ2)

The arithmetic unit 151 performs image processing on the image data group of the wavelength λ1 and the image data group of the wavelength λ2 so that the difference in image characteristics between the image data group of wavelength λ1 obtained in step S200 and the image data group of wavelength λ2 obtained in step S210 is reduced. For example, as processing for reducing the difference in image characteristics between wavelengths, processing of equalizing the maximum value or the minimum value of the image intensity and processing such that the image average and the dispersion of the image intensities of the plurality of wavelengths are nearly equal. In this specification, processing for reducing the difference in image characteristics of image data is referred to as normalization processing.

Here, an example of normalizing the image intensity of the image data will be described. First, the maximum value valmax (one value for all pulses) of the image intensity of the entire pulse volume data obtained in step S200 and step S300 is obtained. Then, the value of 0 or less of the image intensity of the pulse volume data is rounded to zero, and then the image intensities $P_{x,y,z}$ of the voxels of the pulse volume data are normalized so that the maximum value valmax of the obtained image intensity becomes a predetermined value val. That is, the arithmetic unit 151 normalizes the pulse volume data as illustrated in Expression 21.

$$P'_{x,y,z}=P_{x,y,z}*\text{val}/\text{valmax} \quad \text{Expression 21}$$

Here, $P'_{x,y,z}$ are values of the image intensity after normalization of each voxel. Here, the pulse volume data is normalized so that the maximum value of the pulse volume data of a plurality of wavelengths is a predetermined value; however, normalization may be performed so that the maximum value valmax may be obtained for each wavelength and the maximum value valmax becomes equal to the predetermined value val. Furthermore, the minimum value of the pulse volume data may be obtained without rounding the value of 0 or less to 0, the intensity between the minimum value and the maximum value may be converted from 0 to val. Alternatively, the intensity between the minimum and maximum values may be converted from val' to val. In other words, normalization may be performed so that the image intensity falls within a desired numerical range. In addition, as long as the difference in image intensity between wavelengths becomes small, normalization may be performed by any method.

In addition, as another method, the image may be normalized so that the average value of the image intensity becomes 0 or the distribution becomes 1 to be a specific value, or normalization may be performed so that each value does not become 0 or 1, but becomes a specific value.

(Step S900: Step of Obtaining Positional Deviation Information Based on Image Data Processing for Reducing Difference in Image Characteristics)

Based on the image data group of the wavelength λ1 and the wavelength λ2 after performing the processing of reducing the difference in the image characteristics between the wavelengths in step S800, the arithmetic unit 151 obtains positional deviation information corresponding to the irradiation timing with light of the first and second wavelengths. As for the method for obtaining the positional deviation information using the image data, the same method as the method described in step S300 can be adopted.

As described above, by using the image data group in which the difference in the image characteristic between the wavelengths is reduced, it is possible to suppress the deterioration of the estimation accuracy of the positional deviation caused by the difference in the image characteristics between the wavelengths. Then, in step S500, positional deviation correction can be performed with high accuracy by using the positional deviation information obtained in this manner.

In the present exemplary embodiment, an example in which the image data group is generated for each wavelength has been described. However, even in the case where one piece of image data is not generated at one wavelength, as long as an image data group is generated, the method for obtaining positional deviation information described in the present exemplary embodiment can be applied.

Hereinafter, the configuration and processing of the photoacoustic apparatus of the fourth exemplary embodiment will be described. In the fourth exemplary embodiment, the same apparatus as the photoacoustic apparatus of the first, second, or third exemplary embodiment is used. In the fourth exemplary embodiment, the same reference numerals are given to the same components as those of the photoacoustic apparatus of the first, second, or third exemplary embodiment, and a detailed description thereof will be omitted.

In the present exemplary embodiment, an example will be described in which at least one method for obtaining the positional deviation information described in the first, second, or third exemplary embodiment is executed based on an instruction from a user using the input unit 170.

Figure 15:
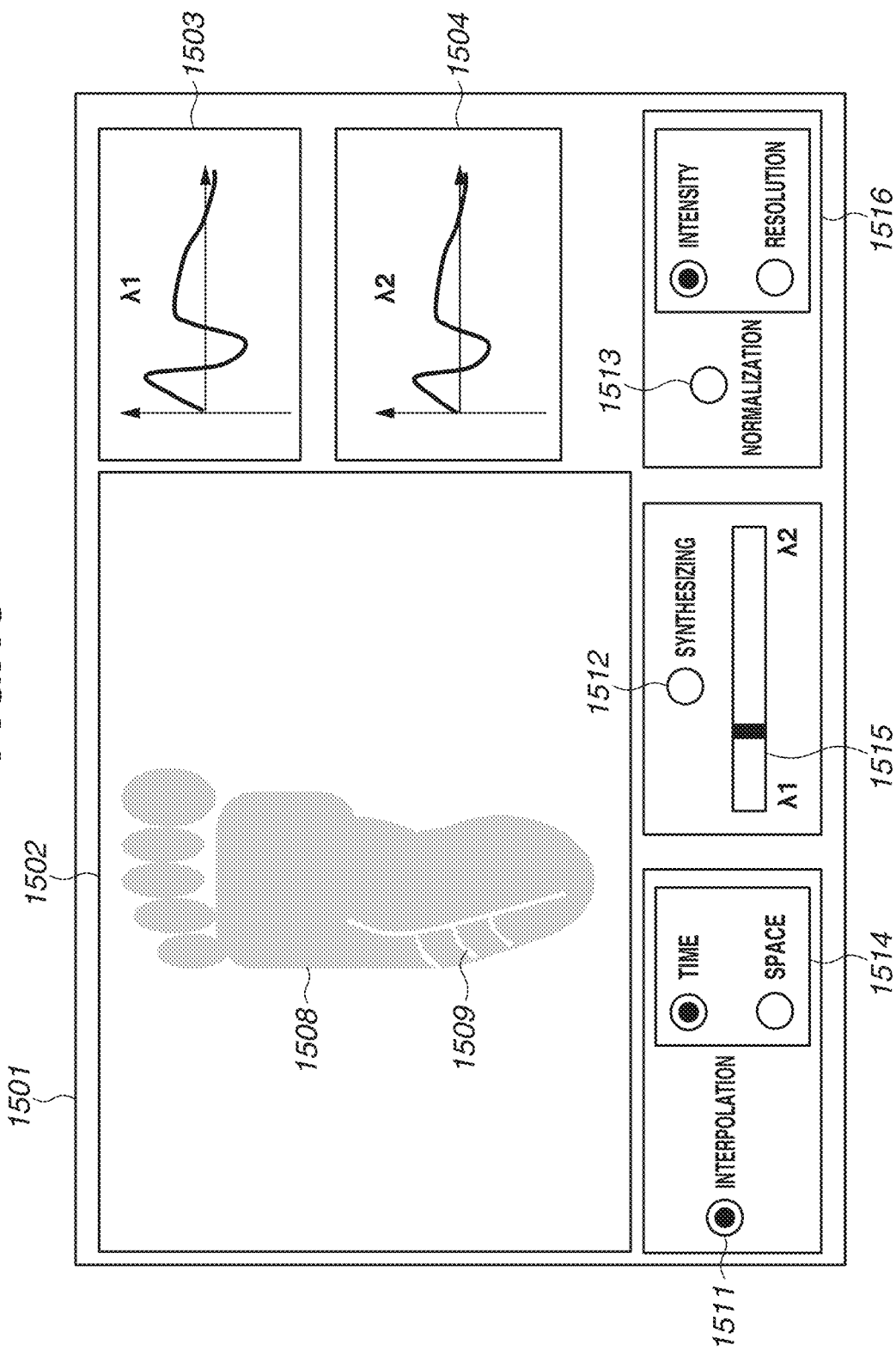
FIG. 15 is a schematic diagram illustrating the GUI according to a fourth exemplary embodiment

FIG. 15 illustrates the GUI displayed on the display unit 160 of the present exemplary embodiment. On a GUI 1501, a display region 1502 of the photoacoustic image, a graph 1503 of the positional deviation amount of the wavelength λ1, and a graph 1504 of the positional deviation amount of the wavelength λ2 are displayed. In the graphs 1503 and 1504, the vertical axis represents the amount of positional deviation and the horizontal axis represents the pulse index. In other words, the graphs 1503 and 1504 plot the positional deviation amount with respect to the pulse volume data at the wavelength λ1 and the wavelength λ2. In FIG. 15, the photoacoustic image 1508 of the foot is displayed in the display region 1502, and a photoacoustic image 1508 includes a blood vessel image 1509.

The user selects a desired obtaining method using the input unit 170 from the buttons 1511, 1512, and 1513 for selecting a method for obtaining positional deviation information.

The selection button 1511 is a button for using the positional deviation information corresponding to the specific wavelength described in the first exemplary embodiment in obtaining the positional deviation information corresponding to the others. In the present exemplary embodiment, when the selection button 1511 is selected, by interpolating the positional deviation information corresponding to the wavelength λ1, a mode is obtained in which positional deviation information corresponding to the wavelength λ2 is obtained. Furthermore, regarding the interpolation method, it is possible for the user to determine whether the arithmetic unit 151 performs temporal interpolation or spatial interpolation by selecting the selection button 1514.

The selection button 1512 is a button for synthesizing positional deviation information corresponding to each of the plurality of wavelengths described in the second exemplary embodiment and updating each positional deviation information. In the present exemplary embodiment, when the selection button 1512 is selected, a mode is obtained in which the positional deviation information corresponding to the wavelength λ1 and the positional deviation information corresponding to the wavelength λ2 are weighted and then synthesized. Furthermore, by operating the slider bar 1515, it is possible for the user to change the weight of each positional deviation information. The function of the slider bar 1515 is the same as that of the slider bar 1007.

The selection button 1513 is a button for obtaining positional deviation information after normalization so as to reduce differences in image characteristics between wavelengths described in the third exemplary embodiment. In the present exemplary embodiment, when the selection button 1513 is selected, a mode is performed in which normalization processing is performed on data obtained based on light of wavelength λ1 and data obtained based on light of wavelength λ2. Furthermore, as to the normalization processing method, the user selects the selection button 1516 so that the arithmetic unit 151 can decide whether to perform normalization processing for reducing the difference in image intensity or normalization processing for reducing the difference in resolution.

As described above, the user selects a method for obtaining desired positional deviation information and confirms the photoacoustic image to which the selected positional deviation information is applied, so that it is possible to confirm the synthesized image data obtained by the method for obtaining the positional deviation information suitable for the characteristics of the image data.

Other Exemplary Embodiment

Furthermore, the present invention can also be realized by executing the following processing. That is, the present invention can be executed by processing in which software (program) for realizing the functions of the above-described exemplary embodiment is supplied to a system or apparatus via a network or various storage media, and a computer (or CPU, micro-processing unit (MPU) or the like) of the system or apparatus reads and executes the program.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2016-188408, filed Sep. 27, 2016, which is hereby incorporated by reference herein in its entirety.

What is claimed is:

1. A photoacoustic apparatus for obtaining image data based on photoacoustic waves, the photoacoustic apparatus comprising:
   an optical end configured to irradiate an object with one of first pulsed light of a first wavelength and second pulsed light of a second wavelength alternately, the first wavelength being different from the second wavelength;
   a receiving unit including a plurality of transducers and configured to receive a first photoacoustic wave and a second photoacoustic wave propagated from the object in response to alternate light irradiation with each one of the first pulsed light and the second pulsed light and output a first reception signal and a second reception signal alternately,
   a processing unit configured to:
   obtain a first image data and a second image data alternately and repeatedly so as to obtain a plurality of the first image data and a plurality of the second image data in association with each of the first pulsed light and the second pulsed light,
   obtain first positional deviation information in association with a relative position of the object with respect to the receiving unit in first irradiation timings of the first pulsed light on the basis of at least two temporally proximal first image data out of the plurality of the first image data, and
   obtain second positional deviation information in association with a relative position of the object with respect to the receiving unit in second irradiation timings of the second pulsed light by temporal or spatial interpolating the first positional deviation information,
   wherein the first positional deviation information is to be obtained without using the second positional deviation information.

2. The photoacoustic apparatus according to claim 1, wherein the processing unit is configured to generate synthesized image data on the basis of the first positional deviation information, the second positional deviation information, the first reception signal and the second reception signal obtained alternately from the receiving unit.

3. The photoacoustic apparatus according to claim 1, wherein the processing unit is configured to:
- obtain the first reception signal and the second reception signal output from the receiving unit receiving the photoacoustic waves generated by irradiating the object with the first pulsed light and the second pulsed light,
- correct positional deviation of the first image data on the basis of the first positional deviation information,
- correct positional deviation of the second image data on the basis of the second positional deviation information, and
- generate synthesized image data on the basis of the first image data and second image data in which positional deviation has been corrected.

4. The photoacoustic apparatus according to claim 1, wherein the processing unit is configured to obtain first position information of the receiving unit associated with the first irradiation timings and generate the first image data group on the basis of the first position information and the plurality of reception signals.

5. The photoacoustic apparatus according to claim 1, wherein the processing unit is configured to:
- obtain the first reception signal and the second reception signal output from the receiving unit in association with the photoacoustic waves due to the first pulsed light and the second pulsed light,
- obtain first position information of the receiving unit associated with the first irradiation timings,
- correct the first position information on the basis of the first positional deviation information,
- obtain second position information of the receiving unit associated with the second irradiation timings,
- correct the second position information based on the second positional deviation information, and
- obtain synthesized image data on the basis of the signal group and the first position information corrected and second position information corrected.

6. The photoacoustic apparatus according to claim 1, wherein the processing unit is configured to generate data indicating a spatial distribution of oxygen saturation as synthesized image data.

7. The photoacoustic apparatus according to claim 1, wherein the first wavelength is a wavelength at which a molar absorption coefficient of oxyhemoglobin and a molar absorption coefficient of deoxyhemoglobin are equal or substantially equal.

8. The photoacoustic apparatus according to claim 1, wherein the processing unit is configured to determine a wavelength of light applied more than a predetermined number of times among the plurality of light irradiations, as the first wavelength.

9. The photoacoustic apparatus according to claim 1, wherein the processing unit is configured to determine a wavelength of most frequently applied light among the plurality of light irradiations, and determine the wavelength as the first wavelength.

10. An information processing method for obtaining image data based on a first photoacoustic wave and a second photoacoustic wave in association with alternate irradiations of first pulsed light of a first wavelength and second pulsed light of a second wavelength which is different from the first wavelength, the information processing method comprising:
- obtaining a first image data and a second image data alternately and repeatedly so as to obtain a plurality of the first image data and a plurality of the second image data in association with the alternate light irradiations with each one the first pulsed light and the second pulsed light;
- obtaining first positional deviation information in association with a relative position of the object with respect to the receiving unit in a plurality of first irradiation timings of the first pulsed light on the basis of at least two temporally proximal first image data out of the plurality of the first image data; and
- obtaining second positional deviation information in association with a relative position of the object with respect to the receiving unit in a plurality of second irradiation timings of the second pulsed light by temporal or spatial interpolating the first positional deviation information,
- wherein the obtaining the first positional deviation information is to be performed without using the second positional deviation information.

11. A non-transitory storage medium storing a program for causing a computer to execute the information processing method for obtaining image data based on a first photoacoustic wave and a second photoacoustic waves in association with alternate irradiations with first pulsed light of a first wavelength and light and second pulsed light of a second wavelength which is different from the first wavelength, the information processing method comprising:
- obtaining a first image data and second image data alternately and repeatedly so as to obtain a plurality of the first image data and a plurality of the second image data in association with the alternate light irradiations with each one of the first pulsed light and the second pulsed;
- obtaining first positional deviation information in association with a relative position of the object with respect to the receiving unit in a plurality of first irradiation timings of the first pulsed light on the basis of at least two temporally proximal first image data out of the first plurality of the first image data; and
- obtaining second positional deviation information in association with a relative position of the object with respect to the receiving unit in a plurality of second irradiation timings of the second pulsed light by temporal or spatial interpolating the first positional deviation information,
- wherein the obtaining the first positional deviation information is to be performed without using the second positional deviation information.

\* \* \* \* \*